US011932947B2

(12) United States Patent
Vidra et al.

(10) Patent No.: US 11,932,947 B2
(45) Date of Patent: *Mar. 19, 2024

(54) COMPOSITION AND METHOD FOR CREATING NANOSCALE SURFACE GEOMETRY ON A COBALT CHROMIUM IMPLANTABLE DEVICE

(71) Applicant: TECH MET, INC., Glassport, PA (US)

(72) Inventors: Michael Vidra, Export, PA (US);
Jordan Incerpi, Pittsburgh, PA (US);
Daniel Jon Schutzer, Irwin, PA (US)

(73) Assignee: Tech Met, Inc., Glassport, PA (US)

( * ) Notice: Subject to any disclaimer, the term of this patent is extended or adjusted under 35 U.S.C. 154(b) by 452 days.

This patent is subject to a terminal disclaimer.

(21) Appl. No.: 17/005,884

(22) Filed: Aug. 28, 2020

(65) Prior Publication Data

US 2021/0062347 A1 Mar. 4, 2021

Related U.S. Application Data

(60) Provisional application No. 62/893,351, filed on Aug. 29, 2019.

(51) Int. Cl.
*C23F 1/26* (2006.01)
*A61F 2/30* (2006.01)
(Continued)

(52) U.S. Cl.
CPC ............ *C23F 1/26* (2013.01); *A61F 2/30767* (2013.01); *A61L 31/022* (2013.01);
(Continued)

(58) Field of Classification Search
CPC ................. C23F 1/26; C23F 1/28; C25F 3/02
See application file for complete search history.

(56) References Cited

U.S. PATENT DOCUMENTS

| 4,376,057 A | 3/1983 | Angelo et al. |
| 5,258,098 A | 11/1993 | Wagner et al. |

(Continued)

OTHER PUBLICATIONS

"Relation Between Normality and Molarity" via https://www.vedantu.com/chemistry/relation-between-molarity-and-normality ; pp. 1-6. (Year: 2023).*

(Continued)

*Primary Examiner* — Binh X Tran
(74) *Attorney, Agent, or Firm* — Dentons Cohen & Grigsby P.C.

(57) ABSTRACT

Compositions and methods for etching an implantable device having a cobalt chrome surface are disclosed. The compositions generally include at least two mineral acids, iron (Fe), and certain component metals of the cobalt chrome to be etched. For example, when etching a cobalt chromium molybdenum alloy, the metals may include chromium (Cr), molybdenum (Mo), and optionally, cobalt (Co). The at least two mineral acids may include hydrochloric acid (HCl), nitric acid ($HNO_3$), and hydrofluoric acid (HF). Alternatively, the composition may be an electrolyte composition useful for electrochemical etching of the implantable device. These compositions and methods may generate nanoscale geometry on the surface of the implantable device to provide implants with improved osseointegration, biocompatibility, and healing after surgery.

18 Claims, 2 Drawing Sheets

(51) Int. Cl.
  *A61L 31/02*    (2006.01)
  *B82Y 5/00*     (2011.01)
  *B82Y 30/00*    (2011.01)
  *B82Y 40/00*    (2011.01)

(52) U.S. Cl.
  CPC .............. *A61F 2002/30925* (2013.01); *A61F 2310/00029* (2013.01); *B82Y 5/00* (2013.01); *B82Y 30/00* (2013.01); *B82Y 40/00* (2013.01)

(56) References Cited

U.S. PATENT DOCUMENTS

| | | | |
|---|---|---|---|
| 5,456,795 | A | 10/1995 | Danjo et al. |
| 5,507,815 | A | 4/1996 | Wagner et al. |
| 6,193,762 | B1 | 2/2001 | Wagner et al. |
| 6,843,929 | B1 | 1/2005 | Farquhar et al. |
| 8,262,737 | B2 | 9/2012 | Bagga et al. |
| 8,496,710 | B2 | 7/2013 | Bagga et al. |
| 8,585,765 | B2 | 11/2013 | Ullrich, Jr. et al. |
| 10,111,753 | B2 | 10/2018 | Patterson et al. |
| 11,053,595 | B2 * | 7/2021 | Vidra .................... C09K 13/12 |
| 2004/0167632 | A1 | 8/2004 | Wen et al. |
| 2006/0085062 | A1 | 4/2006 | Lee et al. |
| 2008/0306554 | A1 | 12/2008 | McKinley |
| 2009/0008365 | A1 | 1/2009 | Tong et al. |
| 2018/0318049 | A1 | 11/2018 | Mandanici et al. |
| 2019/0117827 | A1 * | 4/2019 | Roth .................... A61L 31/022 |
| 2019/0192303 | A1 * | 6/2019 | Gallagher .............. A61P 19/08 |
| 2022/0145474 | A1 * | 5/2022 | Vidra ..................... C25F 3/14 |

OTHER PUBLICATIONS

Koppolu et al., "Osseointegration in Implants: A Review", JRAD Journal of Research and Advancement in Dentistry, Apr. 2, 2014, J Res Adv Dent 2014; 3:3:67-72.

* cited by examiner

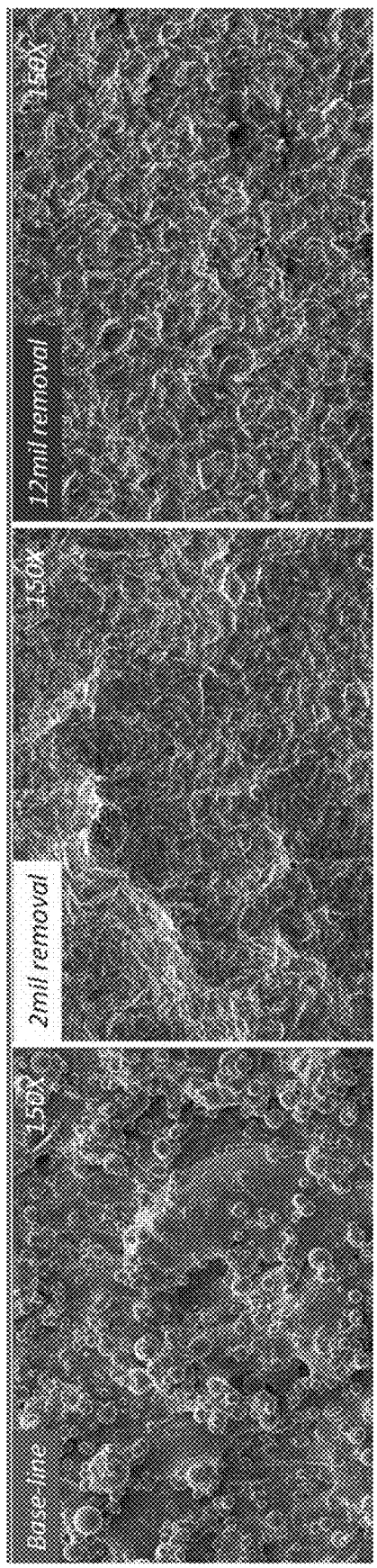
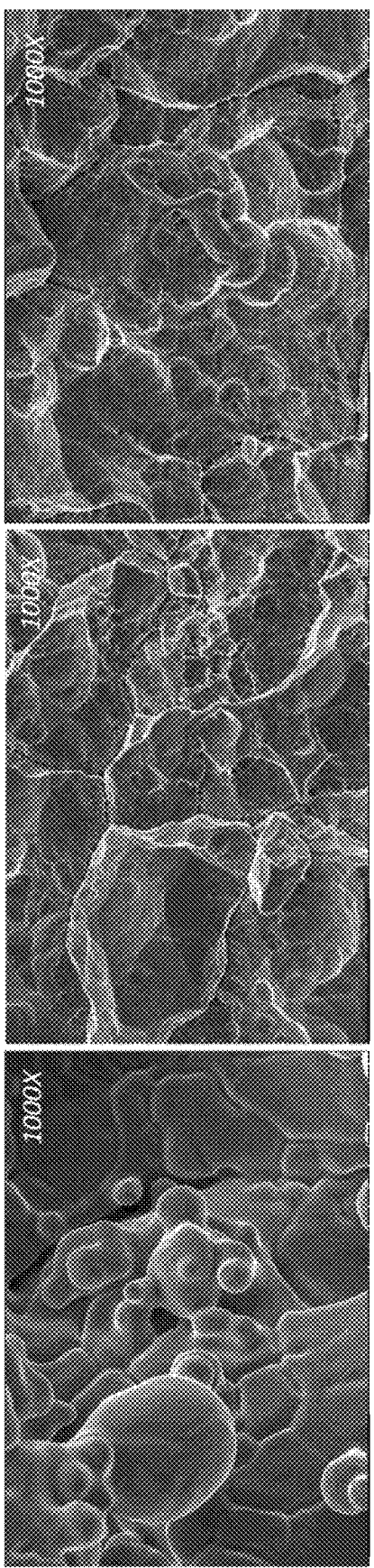
FIG. 1A
FIG. 1B
FIG. 1C
FIG. 1D
FIG. 1E
FIG. 1F

COMPOSITION AND METHOD FOR CREATING NANOSCALE SURFACE GEOMETRY ON A COBALT CHROMIUM IMPLANTABLE DEVICE

CROSS-REFERENCE TO RELATED APPLICATIONS

The present application claims the benefit under 35 U.S.C. § 119(e) of prior U.S. Provisional Application Ser. No. 62/893,351, filed Aug. 29, 2019, the content of which is incorporated by reference here into this application.

TECHNICAL FIELD

This invention pertains generally to methods for creating nanoscale surface geometry on a body implantable device, and more specifically to compositions and methods for etching cobalt chrome surfaces on tissue-contacting and bone-contacting implantable devices.

BACKGROUND

Substantial data exists that strongly suggests manipulation of the material surface of medical implants (orthopedic implants) can influence the rate and characteristics of the body's cellular response to the implant. Moreover, such manipulation has the potential to materially enhance healing and bone growth processes. These surface manipulations are typically performed to create surface features with dimensions (X, Y and Z) in the size range of 20-2,000 nm, although one or more of the dimensions could be much larger, such as with a long narrow ridge of material.

Cobalt chromium alloys, commonly referred to as Cobalt-Chrome (CoCr), are generally corrosion resistant and extremely hard. These outstanding properties result from the crystallographic nature of cobalt, the strengthening effect of chromium and other alloying elements, the formation of extremely hard carbides, and the corrosion resistance imparted by chromium. These qualities make CoCr alloys desirable in the medical field for implantable devices. It also makes the alloys very difficult to chemically mill or chemically machine, by which we mean to intentionally corrode or etch the material in a predictable and controlled manner. Thus, current methods for providing the above indicated surface enhancements that improve integration and healing of cobalt chrome medical implants have typically been mechanical, such as mechanical grit-blasting.

To date, the methods for chemically etching cobalt chromium alloys are limited to mixtures of concentrated hydrogen peroxide and concentrated hydrochloric acid. These methods are expensive and suitable only for superficial removal of material as the mixture is volatile, depletes quickly, and suffers from aggressive metal-ion driven decomposition of the peroxide. Further, this solution commonly results in significant intergranular attack (IGA) of the cobalt chrome surface materials.

Accordingly, there is a need in the art for improved methods for forming nanoscale surface geometry on metal substrates, such as cobalt chrome substrates.

SUMMARY

Described herein are alternate chemistries that address the major drawbacks of the prior art and allow for some adjustment or fine-tuning of surface feature geometries on a substrate. Accordingly, the present invention relates to compositions and methods useful for etching a surface of a cobalt chrome workpiece, such as compositions and methods useful for generating a nanoscale geometry on a cobalt chrome surface of a body implantable device that may provide improved biocompatibility and healing for the device at the implant site, such as improved osseointegration or tissue biocompatibility.

The presently disclosed invention provides a chemical etching composition generally comprising at least two mineral acids, certain component metals of the alloy to be etched, and optionally iron (Fe). For example, when etching a cobalt chromium molybdenum alloy, the component metals may include chromium (Cr), molybdenum (Mo), and optionally, cobalt (Co). The at least two mineral acids may be selected from hydrochloric acid (HCl), nitric acid ($HNO_3$), sulfuric acid ($H_2SO_4$), iodic acid ($HIO_3$), and hydrofluoric acid (HF). According to certain aspects, the at least two mineral acids may comprise hydrochloric acid (HCl), nitric acid ($HNO_3$), and hydrofluoric acid (HF).

According to certain aspects, the composition may comprise 2N to 10N hydrochloric acid (HCl), 0.2N to 0.8N nitric acid ($HNO_3$), and 0.6N to 1.3N hydrofluoric acid (HF). The composition may further comprise 0-300 g/l iron (Fe), 1-170 g/l chromium (Cr), 0.1-40 g/l molybdenum (Mo), and 0 to 355 g/l cobalt (Co). According to certain aspects, the composition may be an aqueous solution.

According to certain aspects, the composition may comprise at least two mineral acids, iron (Fe), and low concentrations of certain component metals of the alloy to be etched. For example, when etching a cobalt chromium molybdenum alloy, the metals may include chromium (Cr), molybdenum (Mo), and optionally, cobalt (Co). According to certain aspects, the composition may comprise 50-300 g/l iron (Fe), 1-10 g/l chromium (Cr), 0.1-5 g/l molybdenum (Mo), and 0 to 10 g/l cobalt (Co).

According to certain aspects, the composition may comprise at least two mineral acids, and high concentrations of component metals of the alloy to be etched. For example, when etching a cobalt chromium molybdenum alloy, the metals may include cobalt (Co), chromium (Cr), and molybdenum (Mo). Exemplary amounts of such metals in the composition include 7 to 355 g/l cobalt (Co), 3-170 g/l chromium (Cr), and 1-40 g/l molybdenum (Mo).

According to certain aspects, the component metals may be included in amounts that mimic the ratio they are included in the metal alloy (i.e., the native ratio of metals in the alloy). For example, when the alloy is a cobalt chromium molybdenum alloy, such as ASTM F75, the component metals may be provided at about 63-68 wt. % Co, 27-30 wt. % Cr, and 5-7 wt. % Mo, based on the total weight of the alloy.

According to certain aspects, the component metals may be included in amounts that mimic the ratio they are included in the metal alloy at a total concentration of 60 g/l to 240 g/l, and may optionally further comprise Fe in amounts of 10 g/l to 300 g/l, such as 10 g/l to 100 g/l. According to certain aspects, the component metal may be Co, Cr, and Mo.

The presently disclosed invention further provides methods for chemical or electrochemical etching of at least a portion of a cobalt chrome surface of a body implantable device, wherein the methods may generate a nanoscale geometry on the at least one surface thereof.

According to a first method, the surface of the implantable device may be etched by any of the chemical etching compositions provided herein. For example, an aqueous chemical etching composition comprising at least two mineral acids, certain component metals of the alloy to be etched, and optionally iron (Fe) may be prepared or provided. For example, the composition may comprise chromium (Cr), molybdenum (Mo), and optionally, cobalt (Co) and/or iron (Fe) as described herein. The surface to be etched is contacted with the aqueous chemical etching composition. According to certain aspects, the surface may be contacted with the chemical etching composition at a temperature of from about 20° C. to about 100° C., such as from about 30° C. to about 100° C., or from about 40° C. to about 100° C., or from about 50° C. to about 100° C., or from about 60° C. to about 100° C. According to yet further aspects, the surface may be contacted with the chemical etching composition at a temperature of from about 65° C. to about 95° C., such as from about 80° C. to about 95° C., such as from about 82° C. to about 88° C., or from about 88° C. to about 91° C. Further, the surface, e.g., the implantable device or portion thereof, may be agitated in the chemical etching composition.

The surface may be contacted with the chemical etching composition for a time period that is unlimited and based on the depth to which the surface is to be etched. According to certain exemplary aspects, the surface may be etched for a time period of from 1 to 1000 minutes, such as 2 to 200 minutes, or even 5 to 50 minutes, or even 20 to 35 minutes.

According to certain aspects of the present invention, the cobalt chrome surface of the implantable device that is to be etched may require an activation step. An exemplary activation step includes exposing the surface that is to be etched to a mineral acid such as a 10% to 100% solution of concentrated hydrochloric acid (v/v; dilution with an aqueous buffer or water). The surface may be exposed to the mineral acid at a range of temperatures, such as room temperature, wherein higher temperatures require lower concentrations of the mineral acid. The alloy material may be exposed to the mineral acid by submersion or spraying.

Immediately after activation, such as within 30 seconds, the activated surface may be exposed to the chemical etching compositions as described herein above. According to certain aspects, the surface may still be "wet" with the activation solution (i.e., mineral acid such as the 10%-100% dilution of hydrochloric acid).

After the surface of the implantable device is activated, it may be etched by contact with the chemical etching compositions, which may include dipping or submersing the surface or the entire implantable device in the composition, or spraying, rolling, or brushing the composition onto one or more surfaces of the work-piece.

Thus, the presently disclosed invention also includes methods for etching a cobalt chrome surface of a body implantable device. According to certain aspects, one method may include preparing one of the chemical etching compositions described above, activating at least the portion of the cobalt chrome surface to be etched with a mineral acid, and contacting the surface with the chemical etching composition. According to certain aspects, the step of contacting with the chemical etching composition may be carried out immediately after the activation step, such as before the activated surface dries (i.e., from exposure to the mineral acid), or within 30 seconds after exposure to the mineral acid.

According to a second method, at least the cobalt chrome surface of the body implantable device that is to be etched may be etched by an electrochemical process, wherein the surface of the implantable device is submerged in an aqueous electrolyte solution. An exemplary aqueous electrolyte solution comprises 0.01M to 10M of one or more metal salts. The surface, submerged in the electrochemical solution, may be exposed to an electric current of 5 Amps/in$^2$ to 100 Amps/in$^2$, such as a current passed through the electrolyte solution between a cathode and an anode wherein the surface acts as the anode or is connected to the anode. The one or more metal salts may be selected from sodium bromide (NaBr), sodium chloride (NaCl), sodium fluoride (NaF), potassium bromide (KBr), potassium chloride (KCl), potassium fluoride (KF), calcium chloride (CaCl$_2$), magnesium chloride (MgCl$_2$), ammonium chloride (NH$_4$Cl), dibasic sodium phosphate (Na$_2$HPO$_4$), monobasic sodium phosphate (NaH$_2$PO$_4$), monobasic potassium phosphate (KH$_2$PO$_4$), dibasic potassium phosphate (K$_2$HPO$_4$), sodium sulfate (Na$_2$SO$_4$), potassium sulfate (K$_2$SO$_4$), ammonium sulfate ((NH$_4$)$_2$SO$_4$) sodium nitrate (NaNO$_3$), potassium nitrate (KNO$_3$), ammonium nitrate (NH$_4$NO$_3$), potassium nitrite (KNO$_2$), and mixtures thereof.

According to certain aspects, either of the methods may further include applying a coating which resists chemical or electrochemical etchants to the implantable device, such as to surfaces that are to be protected from the etchants and/or to form a pattern in the etched surface. According to certain aspects, the method may include removing a portion of the coating to form a patterned design in the coating on the implantable device or to expose a surface on the work-piece; and applying the chemical or electrochemical etching composition according to any of the aspects disclosed herein. According to certain aspects, the method may further comprise stripping the coating from the workpiece after etching is complete. For the chemical and electrochemical etching methods, the coating may be resistant to the chemical etching composition or may be electrically non-conductive, respectively.

The disclosed invention further provides implantable devices having a defined three-dimensional pattern produced using any of the methods and etching compositions disclosed herein. According to certain aspects, the implantable device may be a tissue contacting device, such as a stent or valve (e.g., heart valve), wherein the nanoscale surface provided by the compositions and methods disclosed herein enhance biocompatibility and reduce complications like thrombogenicity and adverse tissue reaction. Enhanced biocompatibility may include enhanced endothelial attachment, proliferation, and restoration of a healthy endothelial surface, and reduced thrombogenicity and adverse localized tissue reaction.

According to certain other aspects, the implantable device may be a bone contacting device, wherein the nanoscale surface provided by the compositions and methods disclosed herein enhance osseointegration. Bone contacting implantable devices include any medical or dental implant for connection to, or positioning adjacent, a bone. For example, surgical bone fixation devices such as wires, nails, pins, screws, staples, rods, and plates, and implants including at least medical implants such as spinal implants, limb prostheses, cochlear prostheses, and dental implants are all implantable devices of the present invention.

BRIEF DESCRIPTION OF THE DRAWINGS

FIGS. 1A-1F show micrographs of cobalt-chromium alloy surfaces, where FIGS. 1A and 1B are 150× and 1000× magnifications, respectively, of a native alloy surface; FIGS. 1C and 1D are 150× and 1000× magnifications, respectively, of a surface etched to 2 mil (50 micron) depth using etch compositions in accordance with certain aspects of the presently disclosed invention; and FIGS. 1E and 1F are 150× and 1000× magnifications, respectively, of a surface etched to 12 mil (300 micron) depth using etch compositions in accordance with certain aspects of the presently disclosed invention.

Figure 2A:
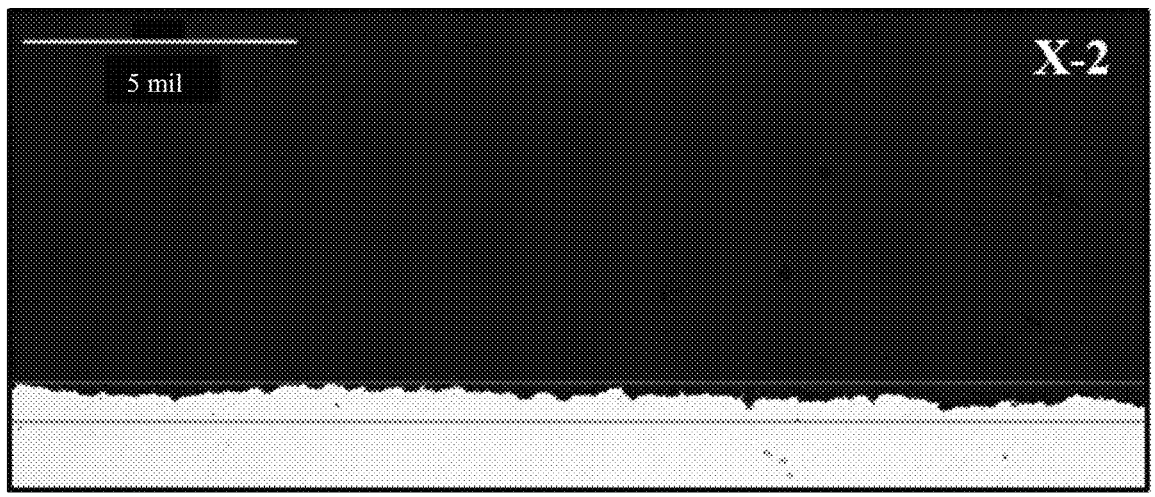

2A-2C show micrographs of a cross-section of a cobalt-chromium-molybdenum alloy surface etched with various chemistries according to certain aspects of the presently disclosed invention, with a 5 mil (127 micron) scale bar.

DETAILED DESCRIPTION

In the following description, the present invention is set forth in the context of various alternative embodiments and implementations involving novel chemistries and methods for generating nanoscale geometry on cobalt chrome surfaces. These novel chemistries and methods are useful for generating nanoscale geometry on tissue and bone contacting surfaces of medical implants. Moreover, medical implants produced using the compositions and methods disclosed herein have improved biocompatibility and healing at the implantation site. While the following description discloses numerous exemplary embodiments, the scope of the present patent application is not limited to the disclosed embodiments, but also encompasses combinations of the disclosed embodiments, as well as modifications to the disclosed embodiments.

Various aspects of the novel chemistry and methods disclosed herein may be illustrated by describing components that are coupled, attached, and/or joined together, or method steps that are linked. As used herein, the terms "coupled", "attached", "linked", and/or "joined" are interchangeably used to indicate either a direct connection between two components or method steps or, where appropriate, an indirect connection to one another through intervening or intermediate components or steps. In contrast, when a component is referred to as being "directly coupled", "directly attached", "directly linked", and/or "directly joined" to another component or method step, there are no intervening elements or steps shown in said examples.

Various aspects of the novel chemistry and methods disclosed herein may be described and illustrated with reference to one or more exemplary implementations. As used herein, the term "exemplary" means "serving as an example, instance, or illustration," and should not necessarily be construed as preferred or advantageous over other variations of the devices, systems, or methods disclosed herein. "Optional" or "optionally" means that the subsequently described event or circumstance may or may not occur, and that the description includes instances where the event occurs and instances where it does not. In addition, the word "comprising" as used herein means "including, but not limited to".

It must also be noted that as used herein and in the appended claims, the singular forms "a", "an", and "the" include the plural reference unless the context clearly dictates otherwise. For example, although reference is made to "a" metal, "an" alloy, and "the" substrate, one or more of any of these components and/or any other components described herein can be used.

Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and appended claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

"Substantially free", as used herein, is understood to mean inclusive of only trace amounts of a constituent. "Trace amounts" are those quantitative levels of a constituent that are barely detectable and provide no benefit to the functional properties of the subject composition, process, or articles formed therefrom. For example, a trace amount may constitute 1.0 wt. %, 0.5 wt. %, 0.1 wt. %, 0.05 wt. %, or even 0.01 wt. % of a component or constituent of any of the etching chemistries disclosed herein. "Totally free", as used herein, is understood to mean completely free of a component or constituent.

As used herein, the terms "implantable device", "device", "substrate", and "workpiece" may be used interchangeably, and may be understood to include a part comprising at least one cobalt chromium metal alloy surface that is to be etched with the compositions according to the methods disclosed herein. The device that is to be etched may be either partly or totally introduced, surgically or medically, into the body of a mammal, such as a human, dog, cat, cow, pig, etc., and is intended to remain there after the procedure. The implantable device may be implanted to replace or repair a part or portion thereof that has worn-out, such as a heart valve or replacement joint, or may be used to ameliorate a condition of the mammal that may benefit for insertion of the implantable device such as a stent. The implantable device may also be useful for sensing a physiological response in vivo or to actuate physiological organs, such as an implantable cardiac defibrillator, pacemaker, cochlear implant, implanted bladder stimulator, implantable wireless pressure sensor, etc.

As used herein, the phrase "defined three-dimensional pattern" generally refers to a nanoscale surface geometry imparted by the chemical etching compositions and methods of the present invention. "Nanoscale surface geometry", as used herein, is understood to mean a surface having topological features with sizes dimensions in the nanoscale range, such as from 1 nm to 5,000 nm, or from 10 nm to 3,000 nm, or from 20 nm to 2,000 nm.

The nanoscale surface geometry of the present invention, when formed on a surface of an implantable device, may enhance the biocompatibility of the device. As used herein, the term "biocompatible" may be understood to mean that the implanted device may have a medically acceptable degree of biocompatibility, i.e., that the device does not induce, or lessens, undesirable side effects within the body of the recipient. These undesirable side effects include blood clotting, tissue death, tumor formation, allergic reactions, foreign body reaction (rejection) and/or inflammatory reactions.

Unless defined otherwise, all technical and scientific terms used herein have the same meanings as commonly understood by one of ordinary skill in the art.

Novel etch chemistries and methods have been developed to address the major drawbacks of the prior art acid etch chemistries, and to allow for adjustment or fine-tuning of surface feature geometries, and may greatly reduce the rates of hydrogen pickup, potential embrittlement, intergranular attack (IGA), and other corrosion of the substrate.

The compositions disclosed herein provide a means for performing a subtractive process on a substrate surface, i.e., chemical or electrochemical etching, also referred to as chemical or electrochemical machining or milling. Chemical etching may comprise, for example, exposure of select surfaces of an object or implantable device, or the entire implantable device, to the chemical etching compositions disclosed herein for a period of time sufficient to remove a portion of the surface to form the desired topographical features (i.e., nanoscale topology). In electrochemical etching, an electric circuit is established with a suitable cathode fixed at a desired distance from the substrate or surface, which acts as the anode. An electrolyte compatible with both anode and cathode materials is introduced between the cathode and anode, and current is passed through the circuit. Metal ions from the exposed portions of the substrate or surface are dissolved or dislocated into the electrolyte at a rate proportional to the current applied.

Chemical Etching Compositions and Methods

According to aspects of the present invention, the chemical etching composition includes at least two mineral acids. A mineral acid is an inorganic acid derived from one or more inorganic compounds. All mineral acids release hydrogen ions when dissolved in water. Suitable examples of mineral acids include, but are not limited to, hydrochloric acid (HCl), nitric acid ($HNO_3$), phosphoric acid ($H_3PO_4$), sulfuric acid ($H_2SO_4$), hydrofluoric acid (HF), iodic acid ($HIO_3$), and hydrobromic acid (HBr).

According to certain aspects of the present invention, the at least two mineral acids in the chemical etching composition are selected from hydrochloric acid (HCl), nitric acid ($HNO_3$), sulfuric acid ($H_2SO_4$), iodic acid ($HIO_3$), and hydrofluoric acid (HF). According to certain aspects, the chemical etching composition comprises hydrochloric acid (HCl), nitric acid ($HNO_3$), and hydrofluoric acid (HF). According to certain other aspects, the chemical etching composition comprises 2N to 10N hydrochloric acid (HCl), 0.2N to 0.8N nitric acid ($HNO_3$), and 0.6N to 1.3N hydrofluoric acid (HF).

According to certain other aspects, the chemical etching composition comprises at least 2N hydrochloric acid (HCl), such as at least 2.5N, or at least 3.0N, or at least 3.5N, or at least 4.0N, or at least 4.5N, or at least 5.0N, or at least 5.5N, or at least 6.0N, or at least 6.5N, or at least 7.0N, or at least 7.5N, or at least 8.0N, or at least 8.5N, or at least 9.0N. According to certain other aspects, the chemical etching composition comprises up to 10N hydrochloric acid (HCl), such as up to 9.6N, or up to 9.0N, or up to 8.5N, or up to 8.0N, or up to 7.5N, or up to 7.0N, or up to 6.5N, or up to 6.0N, or up to 5.5N, or up to 5.0N.

According to certain other aspects, the chemical etching composition comprises at least 0.2N nitric acid ($HNO_3$), such as at least 0.3N, or at least 0.4N, or at least 0.5N, or at least 0.6N, or at least 0.7N. According to certain other aspects, the chemical etching composition comprises up to 0.8 nitric acid ($HNO_3$), such as up to 0.7N, or up to 0.6N, or up to 0.5N, or up to 0.4N, or up to 0.3N.

According to certain other aspects, the chemical etching composition comprises at least 0.6N hydrofluoric acid (HF), such as at least 0.7N, or at least 0.8N, or at least 0.9N, or at least 1.0 N, or at least 1.1N, or at least 1.2N. According to certain other aspects, the chemical etching composition comprises up to 1.3N hydrofluoric acid (HF), such as up to 1.2N, or up to 1.1N, or up to 1.0N, or up to 0.9N, or up to 0.8N, or up to 0.7N.

According to aspects of the present invention, the chemical etching composition also comprises component metals of the metal alloy to be etched. For example, the chemical etching solution may comprise chromium (Cr) and molybdenum (Mo) for use in etching a cobalt chrome workpiece (i.e., implantable device). The chemical etching composition may further comprise iron (Fe). Without being tied to one theory, it is believed that the addition of iron to the chemical etching composition may help to stabilize the reaction rate of the composition and increase its longevity. The chemical etching composition may optionally comprise cobalt (Co).

According to aspects of the present invention, the chemical etching composition may comprise 0-300 iron (Fe), 1-170 chromium (Cr), 0.1-40 molybdenum (Mo), and 0 to 355 g/l cobalt (Co).

According to certain other aspects, the chemical etching composition comprises no iron (Fe), or at least 10 g/l, or at least 20 g/l, or at least 30 g/l, or at least 40 g/l, or at least 60 g/l, or at least 80 g/l, or at least 100 g/l, or at least 120 g/l, or at least 140 g/l, or at least 160 g/l, or at least 180 g/l, or at least 200 g/l, or at least 220 g/l, or at least 240 g/l, or at least 260 g/l, or at least 280 g/l, or at least 300 g/l. According to certain other aspects, the chemical etching composition comprises up to 300 g/l iron (Fe), such as up to 280 g/l, or up to 260 g/l, or up to 240 g/l, or up to 220 g/l, or up to 200 g/l, or up to 180 g/l, or up to 160 g/l, or up to 140 g/l, or up to 120 g/l, or up to 100 g/l, or up to 90 g/l, or up to 80 g/l, or up to 70 g/l, or up to 60 g/l, or up to 50 g/l, or up to 40 g/l, or up to 30 g/l, or up to 20 g/l, or up to 10 g/l.

According to certain other aspects, the chemical etching composition comprises at least 1 g/l chromium (Cr), or at least 2 g/l, or at least 3 g/l, or at least 4 g/l, or at least 5 g/l, or at least 6 g/l, or at least 7 g/l, or at least 8 g/l, or at least 9 g/l, or at least 10 g/l, or at least 20 g/l, or at least 30 g/l, or at least 40 g/l, or at least 50 g/l, or at least 60 g/l, or at least 70 g/l, or at least 80 g/l, or at least 90 g/l, or at least 100 g/l, or at least 110 g/l, or at least 120 g/l, or at least 130 g/l, or at least 140 g/l, or at least 150 g/l, or at least 160 g/l, or at least 170 g/l. According to certain other aspects, the chemical etching composition comprises up to 160 g/l Chromium (Cr), such as up to 150 g/l, or up to 140 g/l, or up to 130 g/l, or up to 120 g/l, or up to 110 g/l, or up to 100 g/l, or up to 90 g/l, or up to 80 g/l, or up to 70 g/l, or up to 60 g/l, or up to 50 g/l, or up to 40 g/l, or up to 30 g/l, or up to 20 g/l, or up to 10 g/l, or up to 8 g/l, or up to 6 g/l.

According to certain other aspects, the chemical etching composition comprises at least 0.1 g/l molybdenum (Mo), or at least 1 g/l, or at least 2 g/l, or at least 3 g/l, or at least 4 g/l, or at least 5 g/l, or at least 6 g/l, or at least 7 g/l, or at least 8 g/l, or at least 9 g/l, or at least 10 g/l, or at least 11 g/l, or at least 12 g/l, or at least 15 g/l, or at least 20 g/l, or at least 25 g/l, or at least 30 g/l, or at least 35 g/l. According to certain other aspects, the chemical etching composition comprises up to 40 g/l molybdenum (Mo), such as up to 35 g/l, or up to 30 g/l, or up to 25 g/l, or up to 20 g/l, or up to 15 g/l, or up to 12 g/l, or up to 11 g/l, or up to 10 g/l, or up to 9 g/l, or up to 8 g/l, or up to 7 g/l, or up to 6 g/l, or up to 5 g/l, or up to 4 g/l, or up to 3 g/l, or up to 2 g/l, or up to 1 g/l.

According to certain other aspects, the chemical etching composition comprises no cobalt (Co), or at least 1 g/l, or at least 2 g/l, or at least 3 g/l, or at least 4 g/l, or at least 5 g/l, or at least 6 g/l, or at least 7 g/l, or at least 8 g/l, or at least 9 g/l, or at least 10 g/l, or at least 20 g/l, or at least 30 g/l, or at least 40 g/l, or at least 50 g/l, or at least 60 g/l, or at least 70 g/l, or at least 80 g/l, or at least 90 g/l, or at least 100 g/l, or at least 110 g/l, or at least 120 g/l, or at least 150 g/l, or at least 200 g/l, or at least 250 g/l, or at least 300 g/l, or at least 350 g/l. According to certain other aspects, the chemical etching composition comprises up to 355 g/l cobalt (Co), such as up to 300 g/l, or up to 250 g/l, or up to 200 g/l, or up to 150 g/l, or up to 120 g/l, or up to 100 g/l, or up to 90 g/l, or up to 80 g/l, or up to 70 g/l, or up to 60 g/l, or up to 50 g/l, or up to 40 g/l, or up to 30 g/l, or up to 20 g/l, or up to 10 g/l, or up to 9 g/l, or up to 8 g/l, or up to 7 g/l, or up to 6 g/l, or up to 5 g/l, or up to 4 g/l, or up to 3 g/l., or up to 2 g/l., or up to 1 g/l.

According to certain aspects, an exemplary chemical etching composition may comprise 2N-10N hydrochloric acid (HCl), 0.05N-0.8N nitric acid ($HNO_3$), and 0.6N-1.3N hydrofluoric acid (HF). For example, the chemical etching composition may comprise 2N-9.6N hydrochloric acid (HCl), 0.05N-0.8N nitric acid ($HNO_3$), and 0.6N-1.3N hydrofluoric acid (HF), or 2N-7.5N hydrochloric acid (HCl), 0.05N-0.8N nitric acid ($HNO_3$), and 0.6N-1.3N hydrofluoric acid (HF), or 2N-5N hydrochloric acid (HCl), 0.05N-0.8N nitric acid ($HNO_3$), and 0.6N-1.3N hydrofluoric acid (HF).

According to certain aspects, the composition may comprise component metals of the metal alloy to be etched, wherein an exemplary chemical etching composition may comprise chromium (Cr), cobalt (Co), and molybdenum (Mo) provided in a native ratio of each metal in the alloy to be etched. For example, the component metals may be provided in a total amount of 60 g/l to 240 g/l in the native ratio of Co:Cr:Mo of the metal alloy. An exemplary metal alloy includes ASTM F75, wherein the component metals are provided at about 63-68 wt. % Co, 27-30 wt. % Cr, and 5-7 wt. % Mo, based on the total weight of the alloy.

According to certain aspects, the component metals may be provided in a total amount of 60 g/l, or 70 g/l, or 80 g/l, or 90 g/l, or 100 g/l, or 110 g/l, or 120 g/l, or 130 g/l, or 140 g/l, or 150 g/l, or 160 g/l, or 170 g/l, or 180 g/l, or 190 g/l, or 200 g/l, or 210 g/l, or 220 g/l, or 230 g/l, or 240 g/l in the native ratio of Co:Cr:Mo of the metal alloy.

According to certain aspects, an exemplary chemical etching composition may comprise 2N-10N hydrochloric acid (HCl), 0.05N-0.8N nitric acid ($HNO_3$), 0.6N-1.3N hydrofluoric acid (HF), 1-170 g/l Chromium (Cr), 0.1-40 g/l molybdenum (Mo), 0-355 g/l cobalt (Co), and 0-300 g/l Iron (Fe).

According to certain aspects, an exemplary chemical etching composition may comprise 2N-9.6N hydrochloric acid (HCl), 0.05N-0.8N nitric acid ($HNO_3$), 0.6N-1.3N hydrofluoric acid (HF), 0-10 g/l cobalt (Co), 1-10 g/l chromium (Cr), 0.1-5 g/l molybdenum (Mo), and 0-125 g/l iron (Fe).

According to certain aspects, an exemplary chemical etching composition may comprise 2N-7.5N hydrochloric acid (HCl), 0.05N-0.8N nitric acid ($HNO_3$), 0.6N-1.3N hydrofluoric acid (HF), 10-170 g/l Chromium (Cr), 2-40 g/l molybdenum (Mo), 7-355 g/l cobalt (Co), and 0-300 g/l Iron (Fe).

According to certain aspects, an exemplary chemical etching composition may comprise 2N-7.5N hydrochloric acid (HCl), 0.05N-0.5N nitric acid ($HNO_3$), 0.6N-1.3N hydrofluoric acid (HF), 50-200 g/l cobalt (Co), 20-60 g/l chromium (Cr), 4-12 g/l molybdenum (Mo), and optionally 10-100 g/l iron (Fe).

According to certain aspects of the present invention, the workpiece may be etched on one or more surfaces by contacting at least one surface, or a portion thereof, of the device with any of the chemical etching compositions disclosed herein. Before the workpiece can be etched with the chemical etching compositions of the presently disclosed invention, the workpiece may require an activation step. An exemplary activation step includes exposing the surface to be etched to a mineral acid such as a 10% to 100% solution of concentrated hydrochloric acid (v/v; dilution with an aqueous buffer or water). The surface may be exposed to the mineral acid at a range of temperatures, such as room temperature, wherein higher temperatures generally require lower concentrations of the mineral acid. The workpiece may be exposed to the mineral acid by submersion or spraying.

Immediately after activation, such as within 120 seconds, or 60 seconds, or 30 seconds, the workpiece may be exposed to the chemical etching compositions as described herein below. According to certain aspects, the device may still be "wet" with the activation solution (i.e., mineral acid such as the 10%-100% dilution of hydrochloric acid).

After the surface of the work-piece is activated, it may be etched by contacting the work-piece with the chemical etching compositions, which may include dipping or submersing the device, or at least a portion of one surface thereof, in the composition, or spraying, rolling, or brushing the composition onto one or more surfaces of the workpiece. For example, the workpiece to be etched may be attached to a fixture resistant to the chemical etch composition and both the workpiece and at least a portion of the fixture may be submerged in the chemical etch composition for a specified time (e.g., the workpiece is suspended over/in the chemical etch composition).

According to certain aspects, the surfaces to be etched may be positioned horizontally or vertically depending on the targeted surface characteristics. Thus, according to certain aspects of the present invention, the implantable device may be etched on one or more surfaces by positioning the device at an angle within the chemical etching composition. Exemplary angles include 0° with respect to the surface of the "bath" containing the chemical etch composition (i.e., horizontal facing upward), to 90° with respect to the surface of the bath (i.e., vertical), to 180° with respect to the surface of the bath (i.e., horizontal facing downward), or any angle therebetween.

Alternatively, the part may be placed into a drum filled with the chemical etch composition, and the drum may be rotated. Additional substrate, such as inert plastic beads or pieces, may be added to the drum to cushion the parts during rotation.

The chemical treating step may include agitating the workpiece in the chemical etching composition (e.g., using the rotating drum discussed above, or by agitating the fixture that is attached to the part). The chemical treating step may include recirculating the etching composition, wherein the recirculating may include circulation of the original chemical etching solution (i.e., etching solution applied/used at start of method), or circulation of the original chemical etching solution with additional new, unused chemical etching solution. The chemical treating step may include exchange of used chemical etching solution after a certain amount of etch time for new, unused chemical etch solution.

The chemical treating step may further include heating the work-piece and/or the chemical etching composition to a temperature in a range of from about 20° C. to about 100° C., such as from about 30° C. to about 95° C., or from about 40° C. to about 95° C., or from about 50° C. to about 95° C., or from about 60° C. to about 95° C., or from about 65° C. to about 95° C., or from about 80° C. to about 90° C., or from about 82° C. to about 88° C. According to certain aspects, the alloy material may be contacted with the chemical etching composition at a temperature in a range of from about 20° C. to about 100° C., such as from about 30° C. to about 95° C., or from about 40° C. to about 95° C., or from about 50° C. to about 95° C., or from about 60° C. to about 95° C., or from about 65° C. to about 95° C., or from about 80° C. to about 90° C., or from about 82° C. to about 95° C., or from about 82° C. to about 91° C., or from about 82° C. to about 88° C.

According to certain aspects, the alloy material may be contacted with the chemical etching composition for an unlimited time period based on the desired depth of etch. Etching starts as soon as the alloy material is exposed to the chemical etching composition and may proceed until the desired depth of etching is achieved. As such, the alloy material may be contacted with the chemical etching compositions from greater than 0 seconds to greater than several hours or days. According to certain aspects of the presently disclosed invention, the alloy material may be exposed to, such as agitated within, the chemical etching composition for a time of from 1 to 1000 minutes, such as from 2 to 200 minutes, or from 5 to 50 minutes.

The chemical etching methods may be used to remove portions or all of a surface of the body implantable device to form the desired nanoscale topological features. Moreover, the compositions and methods disclosed herein provide removal of the material without significant intergranular attack (IGA). The compositions and methods disclosed herein also provide means to remove artifacts of manufacture, such as support structures formed during 3D manufacture of the body implantable device, or islands left behind during laser manufacture of the body implantable device, or to reduce debris from the body implantable device surfaces, such as artifacts of the additive manufacturing process, e.g., powder, particles, granules, etc., that were not completely melted or completely sintered during the additive building. Debris may also include external debris such as dirt or other artifacts of handling.

The chemical etching compositions and methods of the present invention may be used to etch a metal substrate, such as a cobalt chrome substrate, leaving a surface having nanoscale geometry. As mentioned, these inventive compositions and methods allow fine adjustment of the surface geometry by varying the amounts of various components in the composition, and/or the time and temperature of exposure, either in unison or relative to one another. That is, the concentrations of the various components may be raised in unison, such as by addition of components or evaporation; lowered in unison, such as by addition of aqueous solvent; or changed individually. Additionally, the time and temperature of exposure may be varied with changes in the chemistry, or with changes in either of the variables (e.g., increased exposure time at lowered reaction temperatures).

The amount of material removed by the chemical etching composition, i.e., the depth of the etch, is unlimited and may depend on the amount of exposure time to the chemical etching composition and depletion of the chemistry in the composition, e.g., after long exposure times.

The rate of etching, i.e., rate of material removed, may depend on a combination of the proportion of chemical components to one another, the temperature, and/or amount of agitation of the body implantable device in the chemical etching composition. For example, according to certain aspects of the presently disclosed methods, a sample of cobalt chrome may be etched at a rate of 0.1 to 1 mil/minute in the presently disclosed chemical etching compositions, such as 0.3 to 1 mil/minutes, or about 0.5 mil/minute, when exposed at room temperature.

Once etching is complete, the work-piece may be rinsed clean of all residual etchant and, if a coating is present on the work-piece, placed in a bath of stripping solution (a solvent matched to the coatings) to remove all remaining coating material. Alternatively, a wet blast process consisting of a high-pressure spray of a solution containing a suitable aggregate component could be used in place of the stripping solution to mechanically remove the coating from the object. After the remaining coating is removed ("stripping"), the workpiece may be thoroughly pressure-washed and dried in preparation for any required final surface treatments.

One unique and unexpected quality of certain of the etching compositions and methods of the presently disclosed invention is that the final surface, after the chemical etching is completed, may be a passivated surface. That is, the etched workpiece may be resistant to etching a subsequent time. Alternate chemistries and/or mechanical polishing or abrasion may be used to fracture, disrupt, or activate the passivated surface in preparation for a subsequent round of chemical etching using the chemical etching compositions of the present invention.

The presently disclosed compositions and methods, which may provide a passivated surface on a cobalt chrome workpiece, may be particularly useful for workpieces that are medical implants. That is, the passivated surfaces have lower surface reactivity, which may thus lower the overall toxicity of the alloy in the human body.

Passivation may be useful to achieve complex patterning of a surface, where certain areas that are protected during a first round of etching, may be uncoated and etched during a second round of etching to a depth different than the depth of etching achieved during the first round of etching. Such a process may be used to achieve any number of varied depths in a substrate over any number of coating and etching processes. In addition, the resultant surface may be expected to exhibit an even higher degree of corrosion resistance at elevated temperatures than the pre etch base alloy. Accordingly, the present inventors have found that the chemical etching compositions and methods of use thereof provide for unlimited chemical etching or milling of the surface (e.g., depth, total area, etc.) in a single etching process.

Electrochemical Etching Compositions and Methods

An electrochemical etching (EChE) process may be used to provide the nanoscale surface geometry. The device may be submerged in an electrolytic solution and may have a cathode inserted in the solution such that the cathode does not make contact with the device. The electrically conductive device may thus act as the anode, such that when an electric current passes through the electrolyte (between the anode and cathode), the surface of the device is etched, i.e., the current will etch the exposed surface by "plating" the object material, acting as the anode in this case, toward the inserted cathode in an electrochemical etching process. The device may be made electrically conductive by attachment to an anode (i.e., wired in a circuit)

The cathode may be shaped to match the general contour of the surface to maintain constant distance and therefore constant resistance between the cathode and anode, or a simple geometric shaped cathode such as a cylinder may be used and compensated with an insulating coating or cover applied selectively to achieve constant resistance across the cathode-anode gap. Fine tuning of the concentration of electrolyte, current, and temperature may be used so that a standard shaped cathode may remove material in a specific and selected manner.

According to certain aspects of the present invention, the device and the cathode may be placed into a fixture having electrical connection(s) (i.e., electric leads that make contact with or are directly attached to the device and the cathode). The electrolyte solution may be pumped into and through the fixture so that there is a flow of electrolyte solution between the device (i.e., anode) and the cathode (i.e., the anode-cathode gap). According to certain aspects, the cathode may be part of the fixture such that only the body implantable device needs to be positioned within the fixture.

In all cases, the electrolyte solution may be recirculated or circulated so that newly introduced electrolyte may be moved rapidly through the anode-cathode gap and out into an external tank so that the removed material flows out into a settling tank instead of plating to the inserted cathode. Alternatively, the removed material may simply be plated onto the cathode.

Thus, according to certain methods of the presently disclosed invention, the device is exposed to an electrolyte solution comprising an aqueous solution having an electrolyte dissolved therein. The electrolyte may be selected from the group consisting of a water soluble inorganic compound, a water soluble organic compound, an acid, a base, a water soluble oxidizer, an alcohol, a glycol, a glycol ether, an amine, an amide, a pyrrolidone, and mixtures thereof.

According to certain aspects, a preferred electrolyte solution is one that comprises a water-soluble inorganic compound. Any suitable water-soluble inorganic compound can be used to form the electrolyte solution. Suitable water-soluble inorganic compounds include salts of Group Ia, IIa, transition metals, and mixtures thereof. Examples of suitable metal cations include; lithium, sodium, potassium, magnesium, and calcium. According to certain aspects, the water soluble inorganic compound may be selected from the group consisting of chlorides, such as sodium chloride (NaCl), potassium chloride (KCl), calcium chloride (CaCl), magnesium chloride ($MgCl_2$), and ammonium chloride ($NH_4Cl$); phosphates, such as dibasic sodium phosphate ($Na_2HPO_4$), monobasic sodium phosphate ($NaH_2PO_4$), monobasic potassium phosphate ($KH_2PO_4$), and dibasic potassium phosphate ($K_2HPO_4$); sulfates such as sodium sulfate ($Na_2SO_4$), potassium sulfate ($K_2SO_4$), and ammonium sulfate (($NH_4)_2SO_4$); nitrates such as sodium nitrate ($NaNO_3$), potassium nitrate ($KNO_3$), ammonium nitrate ($NH_4NO_3$), and potassium nitrite ($KNO_2$); bromides such as potassium bromide (KBr), sodium bromide (NaBr), ammonium bromide ($NH_4Br$), calcium bromide ($CaBr_2$), and magnesium bromide ($MgBr_2$); fluorides such as sodium fluoride (NaF), potassium fluoride (KF), and lithium fluoride (LiF), magnesium fluoride ($MgF_2$), and calcium fluoride ($CaF_2$); and mixtures thereof. Preferred electrolytes include NaCl, $NaNO_3$, and NaF. Typically, the water soluble inorganic compound is present in the electrolyte solution at a concentration of about 0.01 M to saturation, such as from about 0.05 M to about 10 M, or from a concentration of about 0.05 M to about 5 M, or from a concentration of about 0.05 M to about 3 M.

Water soluble organic compounds can be used in preparing the electrolyte solution. Suitable water soluble organic compounds include carbohydrates, including; tetroses such as erythrose, threose, and erythrulose; pentoses, such as ribose, arabinose, xylose, lyxose, ribulose, and xylulose; hexoses, such as allose, altrose, glucose, mannose, gulose, idose, galactose, talose, psiscose, fructose, sorbose, and tagatose; disaccharides, such as sucrose, lactose, maltose, trehalose, and cellobiose; oligosaccharides; polysaccharides; and mixtures thereof. In a preferred embodiment, the water-soluble organic compound is glucose. Typically, the water-soluble organic compound is present in the electrolyte solution at a concentration of about 0 M to about 5 M, preferably a concentration of about 0.05 M to about 3 M, and more preferably at a concentration of about 0.1 M to about 1 M.

The current and current density may be varied as well as the distance between the anode and the cathode, the concentration and temperature of the electrolytes, and flow rate of the electrolyte. This allows for optimization of the surface geometry at the nanometer scale to maximize cellular response and the rate of bone integration through manipulation of these various factors. By such manipulation, it is possible to create nanoscale surface geometries significantly superior to those of the prior art.

That is, a current may be applied and surface characteristics such as feature height, length and surface density (number of features in a given area) can be manipulated by adjustment of these various parameters. For example, the electrolyte type, i.e., acid, alkaline, alcohol, salt solution, or combinations of the preceding, and the electrolyte concentration may affect characteristics (i.e., depth, pattern, geometry) of the etched surface. According to a preferred embodiment, the electrolyte may be a salt solution, such as a salt solution having some level of acidity (e.g., aqueous solutions of NaCl, $NaNO_3$, and optionally NaF,). In addition, the presence of other organic and/or inorganic additives can directly impact the desired features and their generation on the surface.

As mentioned, the current, current density (rate of metal removal), and voltage may be varied, in addition to the temperature of the electrolyte solution. Such variation may affect the rate and amount of metal removal from the surface of the device (etch depth, which is differentiated over the nanoscale surface geometry). For example, the surface may be milled or removed to a depth of several mil (where 1 mil equals 25,400 nm). Additionally, the flow rate of the electrolyte, flow path of the electrolyte (e.g., flow direction, such as from the anode to the cathode or vice versa, or perpendicular to the plane of the anode and cathode, etc.), and the rate of recirculation of old electrolyte versus addition of new electrolyte may all affect the rate, pattern, and amount of material removed from the surface of the device. Other aspects, such as whether the electrical current is continuous or pulsed (direct) or pulsed (reversing), and the pulse period and duration will also affect the etch characteristics (e.g., surface geometry and pattern).

Finally, the surface design of the cathode tool (e.g., surface roughness, surface features, surface curvature, etc.), and the distance between the electrodes (i.e., the electrolyte gap; from thousandths of an inch to a gap measured in inches) may be varied to change the etch characteristics.

One embodiment that achieves many of the desired surface characteristics on both cobalt chromium and various alloys thereof includes a mixture of one or more of NaCl, $NaNO_3$, NaBr, NaF, KCl, KBr, KF. For example, in an exemplary embodiment, from 0.5 M to 10 M of each of NaCl and $NaNO_3$, and less than 0.5M of NaF, such as 0.01 to 0.5M NaF are included in water to form an aqueous electrolyte solution.

The etching process is generally carried out by submersing the device in the electrolyte solution and passing a current between the cathode and the anode. The device may act as the anode, such as by connection of the anode to the device and positioning of the cathode in the electrolyte solution. The cathode may be positioned a specific distance from the device, i.e., an electrolyte gap. According to certain aspects, the electrolyte gap may be 0.05 to 1 inch (about 1.25 to 25.4 mm), such as 0.1 to 0.5 inches wide (about 2.54 to about 12.7 mm).

The electrochemical etching process is generally carried out at or near room temperature, such as from 15° C. to 30° C., or from 20° C. to 25° C., but elevated or reduced temperatures are also possible. The process may include use of a current density of from 5 to 100 DC Amps/in$^2$ surface, a voltage of 5 to 20 V DC, generally non-pulsed. The electrolyte flow rate, direction and path may vary depending on the product design. In general, a 98+% first pass separation of byproducts from electrolyte can be expected during recirculation of the electrolyte solution.

The amount of metal removed from the surface, i.e., depth of etch, is generally less than about 10 mil (about 254,000 nm), such as less than about 5 mils (about 127,000 nm), or about 0.01 mils to about 5 mils (about 254 nm to about 127,000 nm) and may depend on the amount of exposure time and current, as well as the flow rate and temperature of the electrolyte solution.

Pattern Generation

According to certain aspects of the present invention, portions of the body implantable device may be etched, such as in a pattern. Those portions that are to remain un-etched may be protected from the etching composition using a masking material. Masking materials may include static adhesion films applied to the surfaces to be protected from the chemical etching compositions. Other masking materials may include at least coatings applied to the surfaces to be protected. The exposed, non-masked surfaces may then be etched by exposure to the etching compositions of the present invention.

For objects which are to be etched using a chemical etchant, the coating may be a coating resistant to the chemical etchant. Moreover, for objects that are to be etched using EChE, the coating may be an electrically non-conductive masking material or coating.

Coatings resistant to the chemical etching composition may be applied by any means known in the art, such as at least dipping, pouring, spraying, brushing, or rolling. Exemplary coatings resistant to the chemical etching compositions of the present invention include, for example, maskants from AC Products, such as ADCOAT AC-818.

Depending on the solids content of the selected coating, multiple applications of the coating may be necessary, allowing for sufficient drying time between applications. The coatings used are generally customized to protect the body implantable device from the selected etchant while avoiding any harm to the underlying material of the object.

After each application, the coating may be allowed to cure in a manner which prevents damage to the preceding application, and/or which does not inhibit future applications. The term "cure", as used in connection with a cured coating, means that at least a portion of the components that form the coating are polymerized, cross-linked, or dried to form a hardened film. Curing or drying reactions to form the hardened film may be carried out under ambient conditions, or may be carried out at elevated temperatures, pressures, or in the presence of various gases. For example, the coating may comprise a solvent which may be evaporated to dry or cure the coating. The solvent evaporation may be accelerated by vacuum removal coupled with fresh air or inert gas supply. Depending upon the nature of the chosen coating, heat sources may be used to accelerate drying. Further, for certain coating chemistries, additional processing steps (imaging, hardening, fixing, etc.) may be necessary to make the coating fully resistant to the targeted etching solution.

The coating may be applied in a pattern that exposes the regions of the body implantable device to be etched and covers the regions to be protected. Alternatively, the coating may be applied to a surface and patterned to remove those regions of the coating that are to be etched on the body implantable device. Such removal may be via mechanical scribing and peeling, or by laser ablation, wherein a laser is utilized to remove or ablate the coating in specific regions or patterns. In both cases, a thickness of the coating may be matched to the characteristics of the scribing or laser ablation equipment. In general, the thinnest application that allows for full protection during the chemical etching step is desired, as thinner coatings require less drying time, less coating material, lower laser intensities, and less time stripping the coating after etching is complete. Moreover, for laser ablation processes, colorants or other additives may be added to the coating to improve the ablation process. The colorants and/or additives may be matched to the specific laser type and wavelength.

According to certain aspects, the coating may be a photoresist, wherein the photoresist may be applied to one or more surfaces, or portions thereof, of the device. A photoresist is a photosensitive coating that changes properties when exposed to light, either gaining or losing resistance to attack by an etchant or solvent in the areas exposed to electromagnetic radiation, most commonly in the UV light spectrum. The thickness and properties of the photoresist (e.g., positive or negative photoresist) may be matched to the equipment used for exposure of the pattern onto the photoresist.

While several methods for coating the surface of the body implantable device have been described herein, other methods known in the art are within the scope of the present invention. Furthermore, more than one coating layer may be applied to the surface of the body implantable device, wherein each coating layer may vary in thickness and identity of the coating material. As previously indicated, selection of the specific coating thickness and coating material may depend on at least the method of pattern generation to be used in future steps of the process.

The term "pattern generation" generally describes various methods and implementations used to remove a portion of the coating from the surface of the body implantable device according to a specific pattern or design. The pattern may be preset or programmed into a computer (e.g., translated from CAD drawings) which directs the movements of the various devices used to remove the portion of coating and movements of the body implantable device, either together or individually.

The patterned body implantable device, whether produced through laser ablation, mechanical scribing and peeling, or by a photo resist process may be exposed to the chemical etching composition using any of dipping or submersing the body implantable device in the composition, or rolling, brushing, or spraying the composition onto one or more surfaces thereof. If the body implantable device is contacted with the chemical etching composition in a bath, the device may be agitated while in the bath, or alternatively, the chemical etching solution may be provided as a flow of material (e.g., the device may be positioned in a stream of the chemical etching composition).

For example, the body implantable device to be etched may be attached to a fixture resistant to the chemical etch composition and both the body implantable device and at least a portion of the fixture may be exposed to the chemical etch composition for a specified time (e.g., the part is suspended or submerged in the chemical etch composition, or suspended over the chemical etch composition, such as within a steam of a hot or boiling chemical etch composition).

The present inventors have found that it may be preferred to position the surfaces to be etched horizontally, such as facing upward in the composition, or vertically depending on the targeted surface characteristics. The gaseous byproducts of the etch reaction move directly upwards and away from the surface when that surface is etched horizontally, and do not otherwise affect the process. When the surface to be etched is positioned vertically, bubbles may travel along the vertical surface and influence the etch rate through localized microcirculation and its effects on the replenishment of unreacted chemistry to the target surface. In such ways, surface geometry may be manipulated by adjusting the angle of the parts (with respect to horizontal) during processing.

Thus, according to certain aspects of the present invention, the body implantable device may be etched on one or more surfaces by positioning the body implantable device at an angle within the chemical etching composition. Exemplary angles include 0° with respect to the surface of the "bath" containing the chemical etch composition (i.e., horizontal facing upward), to 90° with respect to the surface of the bath (i.e., vertical), to 180° with respect to the surface of the bath (i.e., horizontal facing downward), or any angle therebetween.

Alternatively, the body implantable device may be placed into a drum filled with the chemical etch composition, and the drum may be rotated. Additional substrate, such as inert plastic beads or pieces, may be added to the drum to cushion the parts during rotation.

The chemical etching step may include agitating the body implantable device in the chemical etching composition. The chemical etching step may include recirculating the etching composition, wherein the recirculating may include circulation of the original chemical etching composition (i.e., etching composition applied/used at start of method), or circulation of the original chemical etching composition with additional new, unused chemical etching composition. The chemical etching step may include exchange of used chemical etching composition after a certain amount of etch time for new, unused chemical etch composition.

Moreover, either or both of the body implantable device and the chemical etching composition may be heated to a temperature in a range of from about 60° C. to about 280° C., such as from about 90° C. to about 250° C., or from about 150° C. to about 225° C., or from about 175° C. to about 200° C.

Alternatively, the patterned body implantable device may be exposed to the electrochemical etching solution, i.e., the aqueous electrolyte solution, and may have a current passed therethrough as described hereinabove. Generally, the body implantable device nay be exposed to the electrolyte solution through submersion in the solution.

The amount of material removed by the etching methods, i.e., depth of etch, is generally less than about 10 mil (about 254,000 nm), such as less than about 5 mils (about 127,000 nm), or about 0.01 mils to about 5 mils (about 250 nm to about 127,000 nm) and may depend on the amount of exposure time to the chemical or electrochemical etching composition and depletion of the chemistry in the composition, e.g., after long exposure times. The upper limit of etch depth depends only on the time, temperature, and chemistry (e.g., ratio and/or concentrations of various components; recirculation or replacement of chemistry) of the etch reaction. For the electrochemical etch process, the etch depth may also depend on factors specific to the electric current generation and/or application, e.g., the voltage, current density, electrolyte gap, etc.

The rate of etching, i.e., rate of material removed, may depend on a combination of the proportion of chemical components to one another, the temperature, the surface being etched (i.e., type of metal), and/or the amount of agitation of the body implantable device in the chemical etching composition, or the flow rate of the circulating etching solution (e.g., electrolyte or chemical etching solution). For example, according to certain aspects of the presently disclosed methods, the body implantable device may be etched at a rate of 0.1 to 1.0 mil/hour (about 30,500 nm). This rate can be greatly accelerated or slowed with changes in the exposure temperature (e.g., temperature of the body implantable device, chemical etch composition, or both during the exposure reaction), and/or the concentration of components of the etch composition (e.g., greater concentration of the components).

Nanoscale Surface Geometry

The nanoscale surface geometry imparted by the compositions and methods of the presently disclosed invention are distinguished from any geometry or pattern that may be applied using the maskants detailed above, or which may be provided on the substrate surface before the etching compositions are applied (e.g., certain implantable devices may comprise surface features provided by chemical or mechanical etching that are micrometers to millimeters in depth; see for example U.S. Pat. Nos. 5,258,098, 5,507,815, and 6,193,762).

Moreover, the nanoscale surface geometry or topography is different from the "depth of etch" described herein, where longer etch times may remove greater amounts of the metal surface (i.e., greater depth of the etch). Longer etch times may be useful to remove artifacts of manufacture, such as support structures formed during 3D manufacture of the body implantable device, or islands left behind during laser manufacture of a body implantable device, or to reduce debris from the body implantable device surfaces, such as artifacts of the additive manufacturing process, e.g., powder, particles, granules, etc., that were not completely melted or completely sintered during the additive building. Debris may also include external debris such as dirt or other artifacts of handling.

Once etching is complete, the body implantable device may be rinsed clean of all residual etchant. According to certain aspect, the body implantable device is substantially free or totally free of residual etchant.

Surface manipulation of a body implantable device is typically performed to create surface features with dimensions (X, Y and Z) in the nanometer range, such as in a size range of 20-2,000 nm, although one or more of the dimensions could be much larger, such as with a long narrow ridge of material.

If the body implantable device was coated on a portion thereof with a maskant or etch resistant coating, the maskant may be removed by placing the device in a bath of stripping solution (a solvent matched to the coatings) to remove all remaining coating material. According to certain aspect, the body implantable device is substantially free or totally free of residual maskant. Alternatively, a wet blast process consisting of a high-pressure spray of a stripping solution could be used in place of the stripping solution to mechanically and chemically remove the coating from the object. After the remaining coating is removed ("stripping"), the body implantable device may be thoroughly pressure-washed or rinsed and dried in preparation for any required final surface treatments, or sterilization prior to packaging for future use.

The chemical and electrochemical etching compositions and methods disclosed herein may provide a regular repeating, though non-identical, pattern having nanoscale geometry on a substrate surface. This pattern is an outcome of the chemical or electrochemical reactions of the inventive compositions disclosed herein and is not the result of a specifically applied pattern. Moreover, while any two areas of the etched surface may have the same surface roughness and topographical features, and thus may appear to have a regular repeating pattern, these patterns are not identical. While the etch depth is indicated above to be on the micrometer scale (e.g., generally less than 1 mil or 25.4 micrometers), the chemical or electrochemical etching compositions provide a geometry on the surface of the device that is on the nanometer scale (i.e., surface roughness and topographical features).

These surfaces have been found to improve osseointegration of the body implantable device. As such, the chemical or electrochemical etching compositions and methods disclosed herein that provide a regular repeating pattern having nanoscale geometry on a substrate surface are useful to produce improved body implantable devices. Such devices can include any bone fixative device or dental implant known in the medical and dental fields. For example, surgical bone fixation devices such as screws, staples, rods, and plates have been in clinical use for decades. These devices largely evolved from industrial designs for fastening wood, steel, plastic and other materials. Starting in the 1950s Per-Ingvar Branemark and others demonstrated that implanted bone fixation devices made of pure titanium had the ability to become permanently incorporated with living bone tissue. The living bone tissue becomes so fused with the titanium oxide layer of the implant that the two cannot be separated without fracture. See, e.g., Macha et al., 2014, Journal of Research and Advancement in Dentistry, *Osseointegration in Implants: A Review*, Vol. 3:67-72.

Alloys made of cobalt, chromium, and molybdenum are strong, have excellent resistance to corrosion, and excellent long-term biocompatibility. Thus, these alloys are well suited for the production of implants that are designed to replace bone and to be load bearing for an extended period, if not permanently.

The compositions and methods disclosed herein provide a roughened surface on a cobalt chrome surface of body implantable devices, wherein the roughened surface has a nanoscale geometry that may further aid in osseointegration and healing after implantation. Without wishing to be bound to one particular theory, the nanoscale geometry may provide pores into which osteoblasts and supporting connective tissue can migrate. Thus, the compositions and methods disclosed herein provide an improved surface on an osteoid implant, such as on a surface that may contact an adjoining surface (i.e., bone), and may help to promote bone growth, fusion, and healing responses. Such implants can include any bone contacting device known in the medical and dental fields, such as a bone fixative device or dental implant. For example, surgical bone fixation devices such as screws, staples, rods, wires, and plates. The irregular surface into which the bone grows creates a natural joinder between the bone and the implant, which maximizes the surface area of the joined element and improves the structural stability and functional connection therebetween. Moreover, the present inventors have found that the nanoscale geometry provided by the presently disclosed compositions and methods stimulate cellular activity, leading to an increase in the rate of bone growth and fusion with the implant.

These surfaces have also been found to improve biocompatibility of tissue contacting implantable devices. For example, stents and valves that have the nanoscale surface geometry reduce the incidence of restenosis. Restenosis occurs when smooth muscle cells in the blood aggregate into clumps and cause the stent to become occluded. While drug-eluting coatings have been used to prevent clumping, recent data has found that these coatings are not a satisfactory solution (i.e., coated stents have been shown to cause blood clots several years after installation). A patient receiving a coated stent must use blood thinners to prevent formation of blood clots that may dislodge from the region of the stent and cause stroke or heart attack. Restenosis of a stent may be largely determined by whether the first layer of cells to grow on the surface of a stent are endothelial cells or smooth muscle cells.

The nanoscale surface geometry of the present invention preferably selects endothelial cells (e.g., from the blood stream) to grow on the inside surface of the stent or stent cover compared to other cell types (e.g., smooth muscle cells). Endothelial cells, as opposed to smooth muscle cells, may 'recognize' the surface structure by pattern matching and adhere. This pattern recognition step is a key element in many molecular biology processes. The implantable devices having nanoscale surface geometry, and the methods and compositions useful for forming the geometry, take advantage of this native molecular biological process to influence the adherence of one type of cell, e.g. endothelial cells, in preference to other types, e.g. smooth muscle cells. Thus, surface nanostructures may be used to selectively enhance adhesion of endothelial cells over smooth muscle cells.

The nanoscale surfaces provided by the compositions and methods disclosed herein are improved over those formed by the prior art acid etch methods. That is, when included on an implant, they demonstrate improved osseointegration and/or biocompatibility of the implant when compared to prior art implants having surfaces formed using acid etch methods. Prior art solutions for improving biocompatibility used coatings, such as nanoporous hydroxyapatite or nanoporous aluminum oxide, to provide improved endothelialization. However, preclinical studies have shown variability regarding the effectiveness of stents coated with nanoporous materials, and nanoparticle debris ejected from the stent surface has been observed. This debris could provoke inflammation and subsequent restenosis.

Accordingly, the present invention provides an improved implantable device comprising a body portion with at least one surface having a defined three-dimensional etched pattern created by the etching compositions and methods of the present invention.

Implantable Devices

The body implantable devices of the presently disclosed invention may be any device that is either partly or totally introduced, surgically or medically, into the body of a mammal, such as a human, dog, cat, cow, pig, etc., and is intended to remain there after the procedure.

Exemplary devices that may comprise the nanoscale surface geometry imparted by the compositions and methods of the presently disclosed invention include medical devices that are tissue contacting, such as an (auxiliary) artificial heart, an artificial valve, a stent, and a pacemaker. In the case of the (auxiliary) artificial heart, examples of the component of the device include a pump casing, an impeller, a shaft constituting the impeller, a rotor and a fin, and an inlet port and an outlet port communicating with the pump casing. The body implantable device may be implanted to replace or repair a part or portion thereof that has worn-out, such as a heart valve or replacement joint, or may be used to ameliorate a condition of the mammal that may benefit from insertion of the implantable device such as a stent. The body implantable device may also be useful for sensing a physiological response in vivo or to actuate physiological organs, such as an implantable cardiac defibrillator, pacemaker, cochlear implant, implanted bladder stimulator, implantable wireless pressure sensor, etc.

Exemplary devices also include any medical or dental implant for connection to, or positioning adjacent, living bone of a patient. For example, surgical bone fixation devices such as screws, staples, rods, and plates, and implants including at least medical implants such as spinal implants, limb prostheses, portions of a joint replacement device, cochlear prostheses, and dental implants.

Restorative implant dentistry generally involves the surgical restoration of one or more teeth in a patient's mouth using an osseointegrative dental implant or anchor that supports a prosthetic tooth (e.g., a porcelain crown), an implant-supported bridge or an implant-supported denture. Dental implants have traditionally been fabricated as a bone-anchoring pin or screw formed from a known osseointegrative material, such as a cobalt chrome alloy. The bone-anchoring portion of the pin or screw is typically configured to extend into an osteotomy formed within the alveolar bone (either the maxilla or the mandible) of a patient. Biological healing and bone tissue growth around the surgical site eventually results in osseointegration (i.e., permanent fixation) of the implant with the living bone tissue surrounding the osteotomy and the implant. Other portions of the implant typically extend through the gingiva into the oral cavity to support one or more prosthetic teeth.

Accordingly, the present invention further provides dental implants comprising a body with at least one surface having a defined three-dimensional pattern created by the chemical or electrochemical etching compositions and methods of the present invention. The at least one surface having the etched pattern is positioned in contact with living bone of a patient, such as an alveolar bone. For example, the dental implant may include a core or anchor portion formed of cobalt chrome, and a head portion that extends from the anchor portion and has an abutment interface. The anchor portion generally includes the surface having a defined three-dimensional pattern disposed about the portion that interfaces with the alveolar bone. After implantation of the implant, such as by screwing or press-fitting the core into the bone (i.e., the osteotomy), bone tissue may osseointegrate into the surface having the defined three-dimensional pattern to anchor the implant in position within the surrounding bone. The head portion may provide an attachment point for the additional portions of the implant (e.g., a porcelain crown or denture).

As described, the anchor portion of the dental implant is positioned within the alveolar bone by press fitting or screwing. As such, the surface of the anchor portion of the dental implant may include either a smooth cylindrical form which is press-fit into a drilled osteotomy, or a threaded form which is threaded into a threaded or unthreaded osteotomy prepared using a bone drill, a bone tap and/or other specialized tools. The geometry of a threaded implant is typically such that it can be inserted into the osteotomy and firmly secured to the surrounding bone tissue via one or more threads which advance into the osteotomy. In a two-stage dental implant, as described above, the anchor and head portions may include addition portions, and may be formed of solid metal such as a cobalt chrome or alloy thereof or may be coated with a layer of cobalt chrome or alloy thereof.

Alternative dental implants include single-stage implants, wherein the tooth or prosthetic is integral with the anchor portion of the implant. In such a case, the entire implant may be formed of a ceramic or other appropriate material for a tooth or prostheses, and the anchor portion may include a coating or layer of solid metal such as cobalt chrome or alloy thereof on a surface thereof, wherein the metal coating includes the defined three-dimensional pattern.

The present invention further provides medical implants such a spinal implant, wherein the implant has a body comprising a surface and connections sized and shaped for placement into an intravertebral disc space. The surface has a defined three-dimensional pattern created by the chemical or electrochemical etching compositions and methods of the present invention. The implant thus provides a surface area of bone-contacting features that allow for and encourage in-growth of bone and proteinaceous materials and biological attachment to a biocompatible material i.e., integration. The three-dimensional surface morphology may incorporate overlapping patterns of features in two dimensions as well as different and independent dimensional depths for each of the features (etched to microscale depths with nanoscale features).

Other exemplary implants include at least prosthetic devices or implants intended for repair of a traumatic bone injury. For example, the chemical or electrochemical etching compositions and methods of the present invention can be applied to at least one surface of an implant intended for connection or replacement of any type of long bone, including the femurs, tibias and fibulas of the legs, the humeri, radii and ulnas of the arms, metacarpals and metatarsals of the hands and feet and the phalanges of the fingers and toes. Implants formed by these methods can be used in the field of prosthetic surgery, for example in case of hip, knee, ankle, shoulder, elbow or finger prostheses or joint replacement. Moreover, implants formed by these methods may find use in craniofacial prosthesis such as an artificial ear (ear prosthesis), maxillofacial reconstruction, eye (orbital prosthesis), or nose (nose prosthesis), bone anchored hearing conduction amplification (i.e., bone anchored hearing aid), and cyborg antenna or "eyeborg," which is a device that is implanted in the skull to perceive color through sound waves (sound conduction through bone).

It is generally believed that the three-dimensional surface of the body implantable device determines its ultimate ability to integrate into the surrounding living bone. Without being limited by theory, it is hypothesized that the cumulative effects of at least implant composition, implant surface energy, and implant surface topography play a major role in the biological response to, and osseointegration of, the body implantable device.

Various implant body shapes may be generated to allow for implantation at various body sites and through various access paths. The structures and surfaces are designed to work in concert to preserve bone structures, and to provide for sufficient bioactivity in each respective location. For example, when the implantable device is a spinal implant, the device may provide stability within the disc space and the graft containment axial column, and the shapes and textures of the bioactive surfaces may vary based on the implant insertion path, location within the disc space, and frictional characteristics of the surfaces. Exemplary spinal implants include those shown in U.S. Pat. Nos. 8,262,737; 8,496,710; 8,585,765; and 10,111,753.

Implantable devices according to the presently disclosed invention may be formed by any of the manufacturing processes known to one of skill in the art. For example, the body implantable device may be formed by a subtractive manufacturing process, such as by direct machining, or may be formed by an additive manufacturing process.

As understood by someone skilled in the art, the term "additive manufacturing" contemplates a manufacturing technology as defined in the international standard ASTM 2792-12. It refers to a process of making useful three-dimensional (3D) objects through a series of sequential steps, forming the shape of the object one layer at a time. Additive manufacturing processes include, but are not limited to, three-dimensional printing (3DP) processes, laser-net-shape manufacturing, direct metal laser sintering (DMLS), direct metal laser melting (DMLM), plasma transferred arc, freeform fabrication, direct digital manufacturing, layered manufacturing, and rapid prototyping. The additive manufacturing method may be selected from, but is not limited to, stereolithography, mask stereolithography, mask projection stereolithography, polymer jetting, scanning laser sintering (SLS), scanning laser melting (SLM), electronic beam melting (EBM), and fused deposition modeling (FDM).

Additive manufacturing technologies comprise processes that create objects by juxtaposition of volume elements according to a pre-determined arrangement that can be defined in a computer aided design file (CAD). Such juxtaposition is the result of sequential operations such as building a material layer on top of a previously obtained material layer and/or juxtaposing a material volume element next to a previously obtained volume element. The 3D CAD models used to define the body implantable devices may be based on standard 3D designs or may be based on 3D representations of the implantation site of the device (i.e., device is specific to a patient). While certain specific methods and manufacturing processes have been mentioned herein, such disclosure should not be understood to limit the methods of forming the body implantable devices or surfaces thereof disclosed herein.

Moreover, the particular etchant reaction conditions and/or maskant utilized for a given attachment surface may be dictated by the base metal utilized for the implant. While a cobalt chrome implant is contemplated as the best mode of practice in the invention, it is to be specifically understood that any base metal etchable with the chemistries disclosed herein may be utilized as the implanted material. A change in the base metal would necessitate a change in the maskant and etchant reaction conditions. No limitation is to be inferred from the selection of cobalt chrome or alloys thereof in the detailed description.

Aspects of the Invention

The following aspects are disclosed herein:

Aspect 1. A composition for etching a nanoscale surface geometry into a cobalt chrome surface of a body implantable device, the composition comprising: at least two mineral acids selected from the groups consisting of hydrochloric acid (HCl), nitric acid (HNO$_3$), sulfuric acid (H$_2$SO$_4$), and hydrofluoric acid (HF); and component metals of the cobalt chromium alloy.

Aspect 2. The composition according to aspect 1, wherein the body implantable device is a bone-contacting device and the nanoscale surface geometry enhances osseointegration when the bone-contacting device is implanted adjacent living bone, or wherein the body implantable device is a tissue-contacting device and the nanoscale surface geometry enhances endothelial attachment and proliferation when the tissue-contacting device is implanted adjacent tissue.

Aspect 3. The composition according any preceding aspect, wherein the at least two mineral acids comprise hydrochloric acid (HCl), nitric acid (HNO$_3$), and hydrofluoric acid (HF).

Aspect 4. The composition according any preceding aspect, comprising: 2N-10N hydrochloric acid (HCl), 0.05N-0.8N nitric acid (HNO$_3$), and 0.6N-1.3N hydrofluoric acid (HF); such as 2N-9.6N hydrochloric acid (HCl), 0.05N-0.8N nitric acid (HNO$_3$), and 0.6N-1.3N hydrofluoric acid (HF); or 2N-7.5N hydrochloric acid (HCl), 0.05N-0.8N nitric acid (HNO$_3$), and 0.6N-1.3N hydrofluoric acid (HF); or 2N-5N hydrochloric acid (HCl), 0.05N-0.8N nitric acid (HNO$_3$), and 0.6N-1.3N hydrofluoric acid (HF).

Aspect 5. The composition according any preceding aspect, wherein the component metals comprise: 1-50 g/l Chromium (Cr); and 0.1-12 g/l molybdenum (Mo).

Aspect 6. The composition according any preceding aspect, further comprising: 0-355 g/l Cobalt (Co), such as 0 g/l to 120 g/l Co, or 0 g/l to 10 g/l Co, or 1 g/l to 10 g/l Co, or 7 g/l to 355 g/l Co.

Aspect 7. The composition according any preceding aspect, further comprising: 0-300 g/l Iron (Fe), such as 10 g/l to 125 g/l Fe, or 50 g/l to 225 g/l Fe.

Aspect 8. The composition according any preceding aspect, comprising 7-355 g/l cobalt (Co); 3-170 g/l chromium (Cr); and 1-40 g/l molybdenum (Mo).

Aspect 9. The composition according any preceding aspect, wherein the component metals comprise Co, Cr, and Mo provided in a native ratio of each metal in the cobalt chromium alloy to be etched.

Aspect 10. The composition according any preceding aspect, wherein the component metals comprise Co, Cr, and Mo provided in a native ratio of each metal in the cobalt chromium alloy to be etched, such as at a total metal content of up to 60 g total Co, Cr, and Mo, or up to 120 g total Co, Cr, and Mo, or up to 180 g total Co, Cr, and Mo, or up to 240 g total Co, Cr, and Mo, or from 60-240 g total Co, Cr, and Mo.

Aspect 11. The composition according any preceding aspect, wherein the composition is an aqueous composition comprising: 2N-10N hydrochloric acid (HCl), 0.05N-0.8N nitric acid (HNO$_3$), 0.6N-1.3N hydrofluoric acid (HF), 1-170 g/l Chromium (Cr), 0.1-40 g/l molybdenum (Mo), 0-355 g/l cobalt (Co), and 0-300 g/l Iron (Fe).

Aspect 12. The composition according to aspect 11, wherein the composition is an aqueous composition comprising: 2N-9.6N hydrochloric acid (HCl), 0.05N-0.8N nitric acid (HNO$_3$), 0.6N-1.3N hydrofluoric acid (HF), 0-10 g/l cobalt (Co), 1-10 g/l chromium (Cr), 0.1-5 g/l molybdenum (Mo), and 0-125 g/l iron (Fe).

Aspect 13. The composition according aspect 11, wherein the composition is an aqueous composition comprising: 2N-7.5N hydrochloric acid (HCl), 0.05N-0.8N nitric acid (HNO$_3$), 0.6N-1.3N hydrofluoric acid (HF), 10-170 g/l Chromium (Cr), 2-40 g/l molybdenum (Mo), 7-355 g/l cobalt (Co), and 0-300 g/l Iron (Fe).

Aspect 14. The composition according aspect 11, wherein the composition is an aqueous composition comprising: 2N-7.5N hydrochloric acid (HCl), 0.05N-0.5N nitric acid (HNO$_3$), 0.6N-1.3N hydrofluoric acid (HF), 50-200 g/l cobalt (Co), 2060 g/l chromium (Cr), 4-12 g/l molybdenum (Mo).

Aspect 15. The composition according aspect 14, wherein the composition further comprises 10-100 g/l iron (Fe).

Aspect 16. A method for etching a nanoscale surface geometry on at least a portion of a cobalt chrome surface of a body implantable device, the method comprising: preparing a chemical etching composition according to any one of aspects 1-15; and contacting at least a portion of the cobalt chrome surface of the implantable device with the chemical etching composition.

Aspect 17. The method according to aspect 16, wherein the step of contacting with the chemical etching composition is performed at a reaction temperature of from about 20° C. to about 100° C.; or at a reaction temperature of from about 82° C. to about 95° C., and wherein the composition etches the surface at a rate of 0.1 to 1.0 mil/minute.

Aspect 18. The method according to aspect 16 or 17, further comprising, before the step of contacting with the chemical etching composition: activating the cobalt chrome surface to be etched with an activation solution comprising a 10% to 100% (v/v) aqueous solution of a mineral acid.

Aspect 19. The method according to aspect 18, wherein the activating is carried out within 120 seconds before the contacting.

Aspect 20. The method according to any one of aspects 16 to 19, wherein the concentrated mineral acid is a 10% to 100% aqueous solution of hydrochloric acid (v/v).

Aspect 21. The method according to any one of aspects 16 to 20, wherein the body implantable device is an implantable bone-contacting device, and wherein the nanoscale surface geometry enhances osseointegration when the bone-contacting device is implanted adjacent living bone; or wherein the body implantable device is an implantable tissue-contacting device, and the nanoscale surface geometry enhances endothelial attachment and proliferation when the tissue-contacting device is implanted adjacent tissue.

Aspect 22. A method for etching a nanoscale geometry into at least a portion of a cobalt chrome surface of a body implantable device, the method comprising: submersing at least the portion of the cobalt chrome surface of the body implantable device in an aqueous electrolyte solution, wherein the aqueous electrolyte solution comprises 0.01M to 10M of one or more metal salts, wherein the one or more metal salts are selected from the group comprising NaBr, NaCl, NaF, NaNO$_3$, NaF, KBr, KCl, and KF; and passing an electric current of 5 Amps/in$^2$ to 100 Amps/in$^2$ through the electrolyte solution between a cathode and an anode, wherein the implantable device acts as the anode or is attached to the anode.

Aspect 23. The method according to aspect 22, wherein the one or more metal salts comprise NaCl, NaNO$_3$, and NaF.

Aspect 24. The method according to aspect 22 or 23, wherein the one or metal salts comprise about 2 M NaCl, about 1.4 M NaNO$_3$, and about 0.6M NaF.

EXAMPLES

Example I

Chemical Etching of a Cobalt Chrome Surface

Surfaces of the cobalt chrome workpiece that are to be etched are first activated by exposure to an activation solution for a short time period at room temperature, such as by submerging (e.g., dipping) or spraying the surface with the activation solution. An exemplary activation solution includes a 10%-100% (v/v) aqueous solution of concentrated hydrochloric acid, although many other mineral acids would provide substantially the same results. While the workpiece is still wet with the activation solution (e.g., within 120 seconds, or 60 seconds, or 30 seconds), it is exposed to the chemical etching compositions using any of the methods disclosed herein.

Because it is preferred to expose the work-piece to the chemical etch composition within a short time after exposure to the activation solution, such as when the work-piece is still wet with the activation solution, it is necessary to apply any coatings or patterning before the activation step. As such, if the workpiece is to be patterned, such as by including a coating to protect certain portions or surfaces of the workpiece, that coating should be applied before the surface is activated and/or etched, and any patterning should be completed before the surface is activated and/or etched.

Provided below are several exemplary chemical etching compositions according to certain aspects of the presently disclosed invention. The compositions were formulated using the following components: acids—31% (w/w) HCl, 67% (w/w) HNO$_3$, 49% (w/w) HF; and metal salts—Iron (III) chloride anhydrous (FeCl$_3$), Cobalt (II) chloride hexahydrate (CoCl$_2$·6H$_2$O), Chromium (III) chloride hexahydrate (CrCl$_3$·6H$_2$O), and Molybdenum (V) chloride anhydrous (MoCl$_5$).

Temperature ranges for the solutions in Tables I-III are from about 20° C. to about 100° C., such as from about 30° C. to about 95° C., or from about 40° C. to about 95° C., or from about 50° C. to about 95° C., or from about 60° C. to about 95° C., or from about 65° C. to about 95° C., or from about 80° C. to about 90° C., or from about 82° C. to about 88° C. Exposure times for the substrate in the chemical etching compositions shown in Tables I-VI may be from greater than 0 seconds up to several hours or days. According to certain preferred aspects, the substrate is exposed to the composition for 1 to 1000 minutes, such as 2 to 200 minutes, or 5 to 50 minutes. According to certain examples, the substrate was exposed to the composition for 5 to 50 minutes or even 20 to 35 minutes.

(A): An exemplary chemical etching composition for the chemical dissolution of a cobalt chrome surface according to certain aspects of the presently disclosed invention include constituents and amounts as shown in Table I.

TABLE I

| Component | Range | Set-Point |
| --- | --- | --- |
| Iron (Fe) | 50-225 g/l | 115 g/l |
| Cobalt (Co) | 0-10 g/l | 0.2 g/l |
| Chromium (Cr) | 1-10 g/l | 3.3 g/l |
| Molybdenum (Mo) | 0.1-5 g/l | 1.2 g/l |
| Hydrochloric Acid (HCl) | 2-10N | 4.0N |
| Nitric Acid (HNO$_3$) | 0.05-0.8N | 0.5N |
| Hydrofluoric Acid (HF) | 0.6-1.3N | 1.0N |

While a cobalt chrome surface can be etched at many (or all) combinations of chemistry within the ranges above, at the set-point conditions indicated in Table I, uniform removal of material at up to 0.015" and beyond was achieved with no measurable IGA.

Removal of material from a cobalt chrome surface using the chemical etch composition and disclosed methods is predictable and repeatable, but unlike most other alloys, once the material is removed, it forms an extremely stable passive surface layer that inhibits further etching without a suitable chemical or electrochemical re-activation of the surface, or disruption of the surface layer (such as by mechanical means, e.g., grit-blasting). Because of this passivation, processing is most easily and economically performed with full targeted removal taking place in one step.

This solution is suitable for Cobalt-Chromium-Molybdenum based alloys such as, but not limited to, ASTM F75 (Standard Specification for Cobalt-28Chromium-6Molybdenum Alloy Casting and Casting Alloy for Surgical Implants), ASTM F799 (Standard Specification for Cobalt-28Chromium-6Molybdenum Alloy Forgings for Surgical Implants), and ASTM F1537 (Standard Specification for Cobalt-28Chromium-6Molybdenum Alloys for Surgical Implants).

This solution is also suitable for Cobalt-Chromium alloys containing Nickel such as ASTM F90 (Standard Specification for Wrought Cobalt-20Chromium-15Tungsten-10Nickel Alloy for Surgical Implant Applications) and ASTM F562 (Standard Specification for Wrought 35Cobalt-35Nickel-20Chromium-10Molybdenum Alloy for Surgical Implant Applications).

(B): An exemplary inventive high-iron composition for etching a cobalt chrome surface is shown in Table II. This composition was found to provide a surface having a nanoscale geometry, wherein an overall surface roughness ($R_a$) of the starting material of approximately 400µ-in (about 10 micrometers, µm) was reduced to a finished condition of approximately 125µ-in (about 3 µm), with a surface material removal of 0.005 inches.

TABLE II

| Component | Range | Set-Point |
|---|---|---|
| Iron (Fe) | 50-300 g/l | 175 g/l |
| Cobalt (Co) | 0-10 g/l | 5 g/l |
| Chromium (Cr) | 1-10 g/l | 3 g/l |
| Molybdenum (Mo) | 0.1-5 g/l | 0.5 g/l |
| Hydrochloric Acid (HCl) | 2-10N | 4.5N |
| Nitric Acid (HNO$_3$) | 0.05-0.8N | 0.11N |
| Hydrofluoric Acid (HF) | 0.6-1.3N | 0.9N |

(C): An exemplary inventive iron-free, high-metals composition for etching a cobalt chrome surface is shown in Table III The composition was found to provide a surface having a nanoscale geometry, wherein an overall surface roughness ($R_a$) of the starting material of approximately 250µ-in (about 6.4 µm) was reduced to a finished condition of approximately 70µ-in (less than 2 µm), with a surface material removal of 0.005 inches.

The higher metals chemical etch composition shown in Table III provides a ratio of metals in solution that is at or near the ratio of the elemental components in the starting alloy, i.e., cobalt chromium molybdenum ASTM F75.

TABLE III

| Component | Range | Set-Point |
|---|---|---|
| Iron (Fe) | 0 g/l | 0 g/l |
| Cobalt (Co) | 7-355 g/l | 81.7 g/l |
| Chromium (Cr) | 3-170 g/l | 35.8 g/l |
| Molybdenum (Mo) | 1-40 g/l | 7.5 g/l |
| Hydrochloric Acid (HCl) | 2-10N | 4.5N |
| Nitric Acid (HNO$_3$) | 0.05-0.8N | 0.11N |
| Hydrofluoric Acid (HF) | 0.6-1.3N | 0.9N |

The present inventors have found that increased metal concentrations reduce the surface roughness (i.e., in the micrometer scale) exponentially up to the point of saturation while providing the nanoscale surface geometry of the presently disclosed invention. Higher concentrations were found to decrease the rate of etch (i.e., as the metal concentrations rise, the rate of etching will begin to decrease, potentially making the processing of parts at or near full saturation impractical from a processing time standpoint).

(D): An exemplary inventive composition comprising component metals in their native ratios for etching a cobalt chrome surface is shown in Table IV. The total metals component of the etching solution is 180 g/l.

TABLE IV

| Component | Range | Set-Point |
|---|---|---|
| Iron (Fe) | 10 g/l-100 g/l | 30 g/l |
| Cobalt (Co) | 117.59 g/l | 180 g/l total component metals |
| Chromium (Cr) | 51.56 g/l | |
| Molybdenum (Mo) | 10.85 g/l | |
| Hydrochloric Acid (HCl) | 2-10N | 5.9N |
| Nitric Acid (HNO$_3$) | 0.05-0.8N | 0.15N |
| Hydrofluoric Acid (HF) | 0.6-1.3N | 0.72N |

The solution was heated to 180° F. (82.2° C.) and the activated substrate was added to the solution, which was maintained at a temperature of 173° F. to 177° F. (78° C. to 80.5° C.). The high metals chemical etch composition shown in Table IV provides a ratio of metals in solution that is at or near the ratio of the elemental components in the starting alloy, cobalt chromium molybdenum ASTM F75.

(E): An exemplary inventive composition comprising component metals in their native ratios for etching a cobalt chrome surface is shown in Table V. The total metals component of the etching solution is 120 g/l.

The solution was heated to 180° F. (82.2° C.) and the activated substrate was added to the solution, which was maintained at a temperature of 173° F. to 177° F. (78° C. to 80.5° C.). The high metals chemical etch composition shown in Table V provides a ratio of metals in solution that is at or near the ratio of the elemental components in the starting alloy, cobalt chromium molybdenum ASTM F75.

TABLE V

| Component | Range | Set-Point |
|---|---|---|
| Iron (Fe) | 10 g/l-100 g/l | 20 g/l |
| Cobalt (Co) | 78.39 g/l | 120 g/l total component metals |
| Chromium (Cr) | 34.37 g/l | |
| Molybdenum (Mo) | 7.24 g/l | |
| Hydrochloric Acid (HCl) | 2-10N | 7.1N |
| Nitric Acid (HNO$_3$) | 0.05-0.8N | 0.156N |
| Hydrofluoric Acid (HF) | 0.6-1.3N | 0.723N |

(F): An exemplary inventive composition comprising component metals in their native ratios for etching a cobalt chrome surface is shown in Table VI. The total metals component of the etching solution is 120 g/l.

TABLE VI

| Component | Range | Set-Point |
|---|---|---|
| Iron (Fe) | 0 g/l-125 g/l | 80 g/l |
| Cobalt (Co) | 78.39 g/l | 120 g/l total component metals |
| Chromium (Cr) | 34.37 g/l | |
| Molybdenum (Mo) | 7.24 g/l | |
| Hydrochloric Acid (HCl) | 2-10N | 7.1N |
| Nitric Acid (HNO$_3$) | 0.05-0.8N | 0.156N |
| Hydrofluoric Acid (HF) | 0.6-1.3N | 0.723N |

The solution was heated to 180° F. (82.2° C.) and the activated substrate was added to the solution, which was maintained at a temperature of 173° F. to 177° F. (78° C. to 80.5° C.). The high metals chemical etch composition shown in Table VI provides a ratio of metals in solution that is at or near the ratio of the elemental components in the starting alloy, cobalt chromium molybdenum ASTM F75.

Superior surface results with increasing metals at the ratios native to the original alloy is an important finding as it provides a processing composition that does not require the addition of non-native metals or metal salts. That is, the composition can be concentrated in metals for improved surface finish simply by etching more material while maintaining the appropriate acid concentrations. This greatly aids process control (i.e., the metals will always drift towards the alloy concentrations with increased usage) and eliminates the need for non-native metals addition, namely iron salts, which represents substantial processing costs in a production setting (e.g., iron solutions need to be made in an inert environment to prevent oxidization of the iron; iron solutions are generally expensive).

Thus, according to certain aspects, a chemical etching composition of the presently disclosed invention may include high concentrations of native metals, up to saturation, at the elemental ratios present in the material of the parts being etched. It should be noted that nitric acid concentrations are relatively low for these compositions as high metals may lead to rapid breakdown of the nitric acid when that acid is present in higher concentrations.

Shown in FIGS. 1A-1F are micrographs of an unetched native cobalt chromium alloy at 150× and 1000× magnification (FIGS. 1A and 1B, respectively) compared with a cobalt chromium alloy surface that has been etched with a composition according to the present disclosure comprising low iron concentration, high chloride and nitrate concentrations, and medium chromium and molybdenum concentrations. The micrographs show 2 mil surface removal (50 microns removed shown at 150× and 1000× magnification in FIGS. 1C and 1D, respectively) and 12 mil surface removal (300 microns removed shown at 150× and 1000× magnification in FIGS. 1E and 1F, respectively). Note that the native surface includes deep crevices, i.e., crevices much deeper than nanoscale, while the etched surfaces according to the present invention lack these crevices and include nanoscale geometry.

Figure 2B:
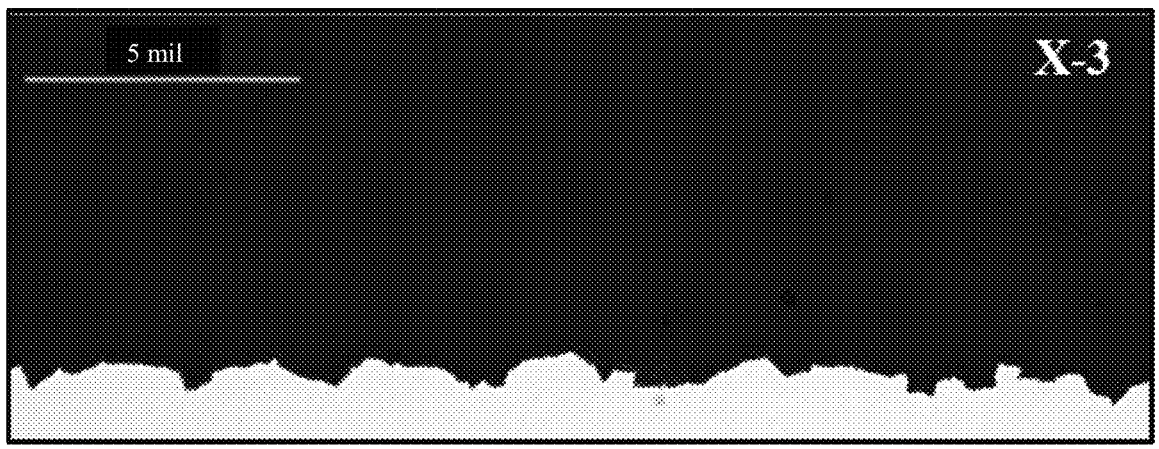
Figure 2C:
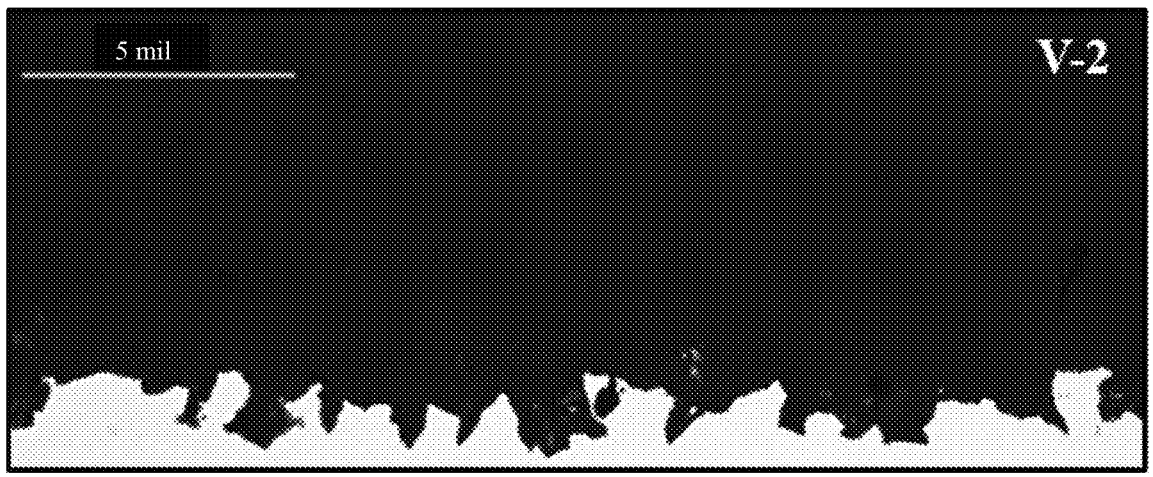

Micrographs of surfaces etched using the compositions and methods of the presently disclosed invention are shown in FIGS. 2A-2C, wherein the smoother surface of FIG. 2A was obtained with an etching composition comprising high iron and chloride concentrations, low nitrate concentration, and medium chromium and molybdenum concentrations; FIG. 2B was obtained with an etching composition comprising medium iron, chloride, and nitrate concentrations, and low chromium and molybdenum concentrations; and FIG. 2C was obtained with an etching composition comprising low iron and chloride concentrations, medium nitrate concentrations, and high chromium and molybdenum concentrations. Note that none of the exemplary surfaces show directional surface scratches or markings (i.e., no extended grooves).

Example II

Electrochemical Etching of a Cobalt Chrome Surface

Desired surface characteristics on various cobalt chromium alloys can also be achieved using an electrolyte solution that includes a mixture of one or more of sodium chloride (NaCl), potassium chloride (KCl), calcium chloride (CaCl$_2$), magnesium chloride (MgCl$_2$), ammonium chloride (NH$_4$Cl), dibasic sodium phosphate (Na$_2$HPO$_4$), monobasic sodium phosphate (NaH$_2$PO$_4$), monobasic potassium phosphate (KH$_2$PO$_4$), dibasic potassium phosphate (K$_2$HPO$_4$), sodium sulfate (Na$_2$SO$_4$), potassium sulfate (K$_2$SO$_4$), ammonium sulfate ((NH$_4$)$_2$SO$_4$), sodium nitrate (NaNO$_3$), potassium nitrate (KNO$_3$), ammonium nitrate (NH$_4$NO$_3$), potassium nitrite (KNO$_2$), potassium bromide (KBr), sodium bromide (NaBr), ammonium bromide (NH$_4$Br), calcium bromide (CaBr$_2$), magnesium bromide (MgBr$_2$), sodium fluoride (NaF), potassium fluoride (KF), lithium fluoride (LiF), magnesium fluoride (MgF$_2$), calcium fluoride (CaF$_2$). Preferred electrolytes include NaCl, NaNO$_3$, and NaF. Typically, the water soluble inorganic compound is present in the electrolyte solution at a concentration of about 0.01 M to saturation, such as from about 0.05 M to about 10 M, or from a concentration of about 0.05 M to about 5 M, or from a concentration of about 0.05 M to about 3 M.

For example, in an exemplary embodiment, from 0.5 M to 10 M of each of NaCl, NaNO$_3$, and NaF are included in water to form the aqueous electrolyte solution. A specific exemplary embodiment is shown in Table II below.

A suitable solution for the electrochemical dissolution of a cobalt chrome surface according to certain aspects of the presently disclosed invention include constituents and amounts thereof as shown in Table II dissolved in deionized water.

TABLE II

| Component | Range | Preferred Set-Point |
| --- | --- | --- |
| NaCl | 0.01-6.5M | 2.0M |
| NaNO$_3$ | 0.01-8.5M | 1.4M |
| NaF | 0.01-0.5M | 0.06M |

While the presently disclosed invention has been described in detail, it should be appreciated by those skilled in the art that various modifications and alternations and applications could be developed in light of the overall teachings of the disclosure. Accordingly, the particular systems and methods disclosed are meant to be illustrative only and not limiting as to the scope of the invention.

What is claimed is:

1. A composition for etching a cobalt chromium surface, the composition comprising:
   hydrochloric acid (HCl), 0.05N-0.8N nitric acid (HNO$_3$), and hydrofluoric acid (HF); and
   at least 3 g/l chromium (Cr), and at least 0.5 g/l molybdenum (Mo),
   wherein the composition etches a nanoscale surface geometry into the cobalt chromium surface of a body implantable device at a rate of 0.1 to 1 mil/minute, and
   wherein the body implantable device is a bone-contacting device and the nanoscale surface geometry enhances osseointegration when the bone-contacting device is implanted adjacent living bone, or
   wherein the body implantable device is a tissue-contacting device and the nanoscale surface geometry enhances endothelial attachment and proliferation when the tissue-contacting device is implanted adjacent tissue.

2. The composition of claim 1, comprising 0.6N-1.3N hydrofluoric acid (HF).

3. The composition of claim 2, comprising:
   2N-10N hydrochloric acid (HCl).

4. The composition of claim 1, comprising:
3-170 g/l chromium (Cr); and
1-40 g/l molybdenum (Mo).

5. The composition of claim 4, further comprising:
1-300 g/l iron (Fe).

6. The composition of claim 4, further comprising:
7-355 g/l cobalt (Co).

7. The composition of claim 1, comprising Co, Cr, and Mo in a native ratio of each metal in the cobalt chromium surface to be etched.

8. The composition of claim 7, comprising 60 g/l-180 g/l total of Co, Cr, and Mo.

9. The composition of claim 8, further comprising 10 g/l-100 g/l Fe.

10. The composition of claim 1, wherein the composition is an aqueous composition comprising:
2N-10N hydrochloric acid (HCl);
0.05N-0.8N nitric acid (HNO$_3$);
0.6N-1.3N hydrofluoric acid (HF);
7-355 g/l cobalt (Co);
3-170 g/l chromium (Cr); and
1-40 g/l molybdenum (Mo).

11. The composition of claim 10, further comprising 10 g/l-100 g/l Fe.

12. A method for etching a nanoscale surface geometry on at least a portion of a cobalt chrome surface of a body implantable device, the method comprising:
contacting at least a portion of the cobalt chromium surface of the implantable device with a chemical etching composition according to claim 1 at a reaction temperature of from about 20° C. to about 100° C.

13. The method of claim 12, wherein the step of contacting with the chemical etching composition is performed at a reaction temperature of from about 82° C. to about 95° C., wherein the composition etches the surface at a rate of 0.1 to 1.0 mil/minute.

14. The method of claim 12, wherein the body implantable device is an implantable bone-contacting device, and wherein the nanoscale surface geometry enhances osseointegration when the bone-contacting device is implanted adjacent living bone.

15. The method of claim 12, wherein the body implantable device is an implantable tissue-contacting device, and the nanoscale surface geometry enhances endothelial attachment and proliferation when the tissue-contacting device is implanted adjacent tissue.

16. The method of claim 12, further comprising, before the step of contacting with the chemical etching composition:
activating the cobalt chromium surface to be etched with an activation solution comprising a 10% to 100% (v/v) aqueous solution of a mineral acid.

17. The method of claim 16, wherein the activating is carried out within 120 seconds before the contacting.

18. The method of claim 16, wherein the concentrated mineral acid is a 10% to 100% aqueous solution of hydrochloric acid (v/v).

* * * * *